United States Patent [19]

Botstein et al.

[11] Patent Number: 4,661,454
[45] Date of Patent: Apr. 28, 1987

[54] GAL1 YEAST PROMOTER LINKED TO NON GALACTOKINASE GENE

[75] Inventors: David Botstein, Brookline, Mass.; Ronald W. Davis, Menlo Park, Calif.; Gerald R. Fink, Brookline, Mass.; Alison Taunton-Rigby, Lincoln, Mass.; Robert G. Knowlton, Lexington, Mass.; Jen-i Mao, Bedford, Mass.; Donald T. Moir, Waltham, Mass.; Christopher G. Goff, Haverford, Pa.

[73] Assignee: Collaborative Research, Inc., Bedford, Mass.

[21] Appl. No.: 470,911

[22] Filed: Feb. 28, 1983

[51] Int. Cl.[4] ............... C12N 1/18; C12N 15/00; C12N 1/00; C07H 15/12
[52] U.S. Cl. ................... 435/256; 435/172.3; 435/942; 435/317; 935/28; 935/37; 935/69; 536/27
[58] Field of Search ............ 435/68, 70, 71, 317, 435/172, 172.3, 255, 256; 536/27; 935/37, 28, 69, 41

[56] References Cited

FOREIGN PATENT DOCUMENTS 0057350 8/1982 European Pat. Off. .
0060057 9/1982 European Pat. Off. ............ 435/172
0068646 1/1983 European Pat. Off. .
0128743 12/1984 European Pat. Off. .
0132309 1/1985 European Pat. Off. .

OTHER PUBLICATIONS

St. John et al., J. Mol. Biol., vol. 152, pp. 285-315, 317-334, Oct. 25, 1981.
Tuite et al., EMBO Journal, vol. 1, No. 5, pp. 603-608, 1982.
Hitzeman et al., Nature, vol. 293, pp. 7171-722, Oct. 29, 1981.
L. Guarente et al., Proc. Natl. Acad. Sci. USA, vol. 79, pp. 7410-7414, Dec. 1982.
St. John et al., Chem. Abstr., vol. 90, No. 21, p. 261.
C. G. Goff et al., Gene, vol. 27, No. 1, Jan. 1984, pp. 35-46.
P. P. Stepien et al., Gene, vol. 24, No. 2/3, Oct. 1983, pp. 289-297.

Primary Examiner—Alvin E. Tanenholtz
Attorney, Agent, or Firm—Wolf, Greenfield & Sacks

[57] ABSTRACT

A DNA segment containing a GAL1 promoter linked to a gene other than the galactokinase gene for directing the expression of the gene within a yeast cell.

5 Claims, 7 Drawing Figures

GAL1 YEAST PROMOTER LINKED TO NON GALACTOKINASE GENE

BACKGROUND OF THE INVENTION

Developments in recombinant DNA technology have enabled the cloning in bacteria of the natural coding sequence of a variety of genes [See Seeburg, P. H., Shine, J., Martial, J. A., Baxter, J. D. and Goodman, H. M., Nature 270, 486–494 (1977) and Shine, J., Seeburg, P. H., Martial, J. A., Baxter J. D. and Goodman, H. M., Nature 270, 494–499 (1977); Keshet, E., Rosner, A., Bernstein, Y., Gorecki, M. and Aviv, H., Nucleic Acids Res. 9, 19 (1981); Miller, W. L., Martial, J. A. and Baxter, J. D., J. Biol. Chem. 255, 7521–7524 (1980)]. Recently, recombinant DNA techniques have been described in which a foreign protein is cloned and expressed in yeast. Evidence for foreign gene expression in yeast came from studies on the in vivo transcription of a rabbit globin gene introduced into Saccharomyces cerevisiae on a yeast plasmid vector. [See Beggs, J. D., van den Berg, J., van Obyen, A., and Weissmann, C., Nature 283, 835–840 (1980).]

In an attempt to maximize expression of foreign genes in yeast, their 5'-promoter region, translation start and signal peptide sequences were replaced with similar regions from the yeast genome. With bovine growth hormone, these regions were replaced with those from the yeast alcohol dehydrogenase (ADH1) gene. Full length, biologically active bovine growth hormone molecules were produced in yeast. [See Hitzeman, R. A., Hagie, F. E., Levine, H. L., Goeddel, D. V., Ammerer, G., and Hall, B. D., Nature 295, 717–722 (1981).] Other promoters were employed but demonstrated much less gene expression. The ability of having a single strong promoter is highly useful to permit the attainment of substantial levels of expression for a variety of genes in yeast.

It has now been discovered that promoters for the GAL1 galactokinase gene are such a promoter. In addition, these promoters are under glucose repression. Thus, it becomes practical to clone any one of a variety of genes including bovine growth hormone, interferon, pre-prorennin and prorennin in yeast with expression maximized by direction of a yeast GAL1 promoter.

SUMMARY OF THE INVENTION

It is an object of the present invention to provide genetic recombinant material carrying a GAL1 promoter of the yeast galactokinase gene for use in expressing a desired protein.

Another object of the present invention is to provide a DNA segment containing a GAL1 promoter linked to a gene other than the galactokinase gene for directing the expression of the gene in a yeast cell.

It is a further object of the present invention to provide a method of expressing bovine growth hormone, interferon, prorennin, pre-prorennin or other polypeptides in a yeast cell by use of a GAL1 promoter linked to the corresponding bovine growth hormone gene, interferon gene, prorennin gene, pre-prorennin gene or other gene.

It is an additional object of the present invention to provide modified strains of Saccharomyces cerevisiae which produce desired polypeptide product under the control of a GAL1 promoter of the yeast galactokinase gene.

A further object of the present invention is to provide a method of producing products such as bovine growth hormone, interferon, prorennin, and pre-prorennin in yeast through recombinant DNA techniques employing a GAL1 promoter.

According to the present invention, the expression of a gene for a desired polypeptide product is controlled by a GAL1 promoter of a yeast strain such as Saccharomyces cerevisiae. The GAL1 promoter is a DNA segment that contains the transcription start signal for galactokinase in yeast. The sequencing information for the GAL1 promoter is shown in Table 1.

TABLE 1

LISTING OF THE SEQUENCE GAL125 AND GAL126

```
         10        20        30        40        50        60        70
GAATTCOACAGGTTATCAGCAACACAGTCATATCCATTCTCAATTAGCTCTACCACAGTGTGTGAACCAA 80        90       100       110       120       130       140
TGTATCCAGCACCACCTGTAACCAAAACAATTTTAGAAGTACTTTCACTTTGTAACTGAGCTGTCATTTAT 150       160       170       180       190       200       210
CTCGTCTTTTCAAAAATTCTTACTTTTTTTTTTGGATGGACGCAAAGAAGTTTAATAATCATATTACATGG 220       230       240       250       260       270       280
CATTACCACCATATACATATCCATATACATATCCATATCTAATCTACTATATGTTGTGGTATGTAAAGAG 290       300       310       320       330       340       350
CCCCATTATCTTAGCCTAAAAAAACCTTCTCTTTGGAACTTTCAGTAATACGCTTAACTGCTCATTGCTA 360       370       380       390       400       410       420
TATTGAAGTACGGATTAGAAGCCGCCGAGCGGGTGACAGCCCTCCGAAGGAAGACTCTCCTCCGTGCGTC 430       440       450       460       470       480       490
CTCGTTTCACCGGTCGCGTTCCTGAAACGCAGATGTGCCTCGCGCCGCACTGCTCCGAACAATAAAGAT 500       510       520       530       540       550       560
TCTACAATACTAGCTTTTATGGTTATGAAGAGGAAAAATTGGCAGTAACCTGGCCCCACAAACCTTCAA 570       580       590       600       610       620       630
ATGAACGAATCAAATTAACAACCATAGGATGATAATGCGATTAGTTTTTTAGCCTTATTTCTGGGGTAATT 640       650       660       670       680       690       700
AATCAGCGAAGCGATGATTTTTGATCTATTAACAGATATATAAATGCAAAAACTGCATAACCACTTTAAC
```

TABLE 1-continued
LISTING OF THE SEQUENCE GAL125 AND GAL126

```
      710         720         730         740      ┌126   750         760         770
TAATACTTTCAACATTTTCGGTTTGTATTACTTCTTATTC │ AAATGTAATAAAAGTATCAACAAAAAATTG
                                                  └CTCTACCGGATCC 780         790         800         810         820 830 840 850 860 870 880
TTAATATACCTCTATACTTTAACGTCAAGGAGAAAAAACCCCGGATCC┐
                                                                    125
```

A DNA segment is provided which contains a GAL1 promoter linked to a gene foreign to the yeast genome for directing the expression of the gene within a yeast cell. The segment is preferably a 0.755 or 0.82 kilobase DNA sequence from the yeast genome that contains signals for transcription of the GAL1 gene into mRNA and subsequent translation of the mRNA. The coding sequence for galactokinase is not present in this DNA fragment.

In a method for obtaining expression of a desired polypeptide product in yeast, a yeast GAL1 promoter is inserted in vitro in front of the gene for that polypeptide product which is contained in a chromosome or plasmid. These vectors are used to transform cells and this new genetic information is maintained in the cell and passed on to its progeny.

Synthesis of a polypeptide product using a GAL1 promoter is advantageous for several reasons:

GAL1 promoters are strong, leading to synthesis of significant amounts of polypeptide product.

the GAL1 promoter activity can be regulated by changing the yeast's carbon source permiting propagation of the yeast without the potentially deleterious effects of polypeptide production, since overly high levels of the product may be toxic to cells.

construction of a yeast strain with these properties is particularly desirable for commercial production of polypeptide products because of existing large-scale yeast fermentation technology and also because of the low toxicity of S. cerevisiae.

DESCRIPTION OF THE PREFERRED EMBODIMENT

Figure 1:
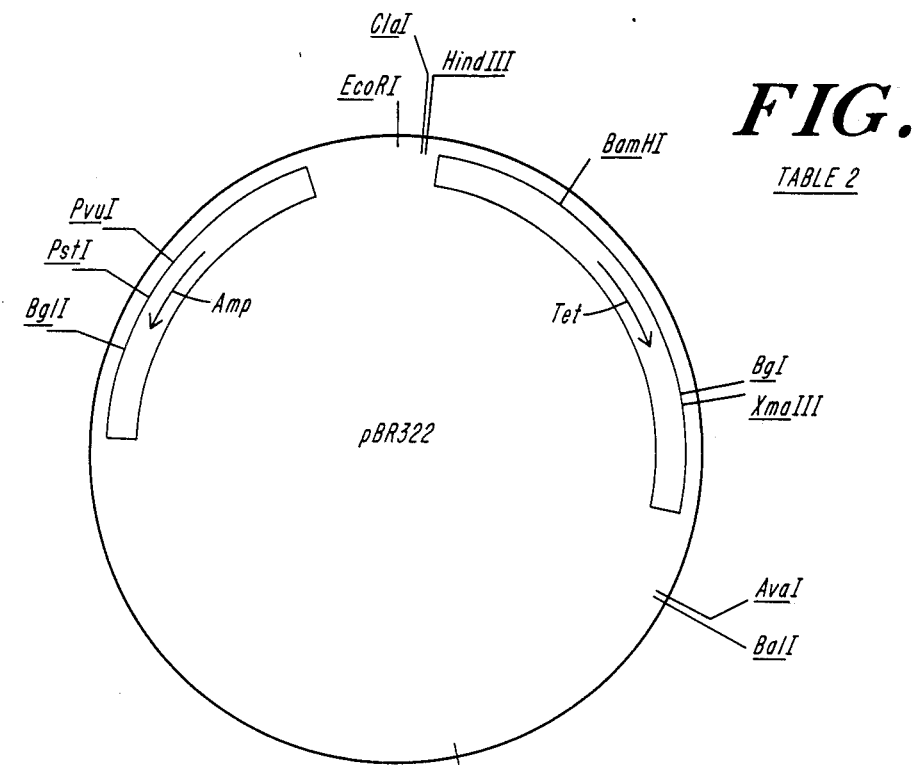

Microorganisms prepared by the genetic engineering processes described herein are exemplified by cultures now on deposit with the American Type Culture Collection, 12301 Parklawn Drive, Rockville, Md. These cultures were deposited by Collaborative Research, Inc. and are identified as follows:

Accession Number 20643, Strain Designation CGY196, deposited September, 1982;

Accession Number 20661, Strain Designation CGY457, deposited February, 1983;

Accession Number 20662, Strain Designation CGY461, deposited February, 1983;

Accession Number 20663, Strain Designation CGY528, deposited February, 1983;

As more fully described below, a particular DNA segment is linked to a gene foreign to the yeast genome and incorporated in a modified strain of *Saccharomyces cerevisiae so that it produces a polypeptide product under the control of a GAL1 promoter of the yeast galactokinase gene. The S. cerevisiae is genetically transformed* with a novel recombinant DNA plasmid. The plasmid was constructed by ligation of DNA segments from the E. coli plasmid pBR322, yeast genomic and plasmid DNA's, and synthetic DNA linkers. The construction of plasmid pBR322, sequenced by J. G. Sutcliffe, *Cold Spring Harbor Symposium* 43, 77–90 (1979), is shown diagrammatically in FIG. 1.

Generally, in preparing the plasmid for joining with the exogenous gene, a wide variety of techniques can be used, including the formation of or introduction of cohesive termini. Blunt ends can be joined. Alternatively, the plasmid and gene may be cleaved in such a manner that the two chains are cleaved at different sites to leave extensions at each end which serve as cohesive termini. Cohesive termini may also be introduced by removing nucleic acids from the opposite ends of the two chains or alternatively, introducing nucleic acids at opposite ends of the two chains. Methods which may be employed in joining cleaved DNA segments depend on the nature of the termini, as described below.

"Blunt-ended" refers to DNA molecules with duplex base-paired termini. (See Sgaramella, V., van de Sande, J. H., and Khorana, H. G., *Proc. Nat. Acad. Sci. USA* 67, 1468–1475 (1970).) The DNA blunt-end termini may be joined by T4 DNA ligase with an apparent $K_m$ of about 50 $\mu$M DNA 5'-ends. (Sugino, A., Goodman, H. M., Heyneker, H. L., Shine, I., Boyer, H. W., and Cozzarelli, N. R., *J. Biol. Chem.* 252, 3987–3994 (1977).)

Blunt-ended DNA's are produced as for example, by cleavage with any of a number of restriction endonucleases, such as HaeIII. Alternatively, random shear breakage or a restriction enzyme making staggered cuts, such as EcoRI, HindIII, or BamHI, may be used, but the DNA termini must then be made blunt by biochemical methods. Such biochemical methods include incubation with single-strand-specific nuclease S1, as described in the following articles: Ulbrich, A., Shine, J., Chirgwin, J., Pictet, R., Tischer, E., Rutter, W. J., and Goodman, H. M., *Science* 196, 1313 (1977); Maniatis, T., Hardison, R. C., Lacy, E., Lauer, G., O'Connell, C., Guon, D., Sim, G. K., and Efstratiadis, A., *Cell* 15, 687 (1978); Scheller, R. H., Thomas, T. L., Lee, A. S., Klein, W. H., Niles, W. D., Britten, R. J., and Davidson, H., *Science* 196, 197 (1977); and Charnay, P., Perricaudet, M., Galibert, F., and Tiollais, P., *Nucleic Acids Res.* 5, 4479 (1978). Alternatively, blunt termini can be created by incubation with T4 DNA polymerase [see Itakura, K., Hirose, T., Crea, R., Riggs, A. D., Heyneker, H. L., Bolivar, F., and Boyer, H. W., *Science* 198, 1056 (1977); and Fraser, T. H., and Bruce, B. J., *Proc. Nat. Acad. Sci. USA* 75, 5936 (1978)], E. coli DNA polymerase [see Seeburg, P. H., Shine, J., Martial, J. A., Baxter, J. D., and Goodman, H. M., *Nature* 270, 486 (1977); Heffron, F., So, M., and McCarthy, B. J., *Proc. Nat. Acad. Sci USA* 75, 6012 (1978); and Backman, K., Ptashne, M. and Gilbert, W., *Proc. Nat. Acad. Sci. USA* 73, 4174 (1976)], and reverse transcriptase [see Ulbrich, A., Shine, J., Chirgwin, J., Pictet, R., Tischer, E., Rutter, W. J., and Goodman, H. M., *Science* 196, 1313 (1977)] with added deoxynucleotide triphosphates.

"Cohesive-ended" refers to DNA molecules with single-stranded termini. The single-stranded extensions are complementary and antiparallel. (See Mertz, J. E., and Davis, R. W., *Proc. Nat. Acad. Sci. USA* 69, 3370-3374 (1972).)

Joining of base-paired duplexes occurs when the nucleoside at a 5'-end carries a phosphate group and the complementary nucleoside opposite to it carries a free 3'-hydroxyl group. Two phosphodiester bonds would be made essentially simultaneously and the joined duplexes would have their nucleotide sequence inverted with respect to one another There are three general approaches to creating cohesive-ends on DNA:

1. digest DNA with type II restriction endonucleases that introduce staggered scissions at unique sequences;
2. treat linear DNA molecules with terminal deoxynucleotidyl transferase to generate single-stranded tails of either poly(dA) and poly(dT) or poly(dC) and poly(dG) at the 3'-hydroxyl terminus of different populations of DNA molecules; and
3. add to blunt-ended molecules linkers, which are short duplexes containing a restricton endonuclease cleavage site. Such linkers are joined to DNA by T4 DNA-ligase catalyzed blunt-end joining. After digesting the product with the restriction enzyme that cleaves the linker, the DNA is terminated with cohesive ends.

These methods are well known, as exemplified in the following articles: Sadler, J. R., Betz, J. L., Teiklenburg, M., Goeddel, D. V., Yansura, D. G., and Caruthers, M. H., *Gene* 3, 211 (1978); Bahl, C. P., Marians, K. J., Wu, R., Stawinsky, J., and Narang, S. A., *Gene* 1, 81 (1976); and Scheller, R. H., Dickerson, R. E., Boyer, H. W., Riggs, A. D., and Itakura, K., *Science* 196, 177 (1977).

"Linker" refers to a duplex, blunt-ended DNA molecule from 6-14 base pairs in length, containing the recognition site for a restriction endonuclease that produces cohesive termini.

In the preferred embodiment of the present invention, the plasmid serves as the vehicle for introduction of the foreign gene into the yeast cell. However, it is not necessary to use a plasmid, since any molecule capable of replication in yeast can be employed. The DNA molecule can be attached to a vector other than a plasmid, which can be a virus or cosmid as known in the art; or it can be integrated into the chromosome.

The recombinant plasmid or plasmid chimera is constructed in vitro. Since the annealing and ligation process not only results in the formation of the recombinant plasmid, but also in the recircularization of the plasmid vehicle, a mixture of ligation products is obtained involving the original plasmid and the foreign DNA. Only the original plasmid and the DNA chimera consisting of the plasmid vehicle and linked foreign DNA will normally be capable of replication. When the mixture is employed for transformation of the bacteria, replication of both the plasmid vehicle genotype and the foreign genotype will occur.

The transformation of the bacterial cells will result in a mixture of bacterial cells, the dominant proportion of which will not be transformed. Of the fraction of cells which are transformed, some significant proportion, but in some cases a minor proportion, will have been transformed by recombinant plasmid. In any event, only a very small fraction of the total number of cells which are present will have the desired phenotypic characteristics.

In order to isolate only the bacteria containing the DNA chimera or the original plasmid, a selectable genetic marker is included on the original plasmid, such as resistance to an antibiotic or heavy metal. The cells can then be grown on an agar medium containing the growth inhibiting substance. Since *E. coli* is used as the bacteria for transformation in the present invention, ampicillin is used as the growth inhibiting material to afford selection in *E. coli*. Only available cells having the resistant genotype will survive. If the foreign gene does not provide a phenotypical property, which allows for distinction between the cells transformed by the plasmid vehicle and the cells transformed by the plasmid chimera, a further step is necessary to isolate the replicated plasmid chimera from the replicated plasmid vehicle. The steps include lysing of the cells and isolation and separation of the DNA by conventional means or random selection of transformed bacteria and characterization of DNA from such transformants to determine which cells contain molecular chimeras. This is accomplished by physically characterizing the DNA by electrophoresis, gradient centrifugation, sequence analysis or electron microscopy.

Cells from various clones may be harvested and the plasmid DNA isolated from these transformants. The plasmid DNA may then be analyzed in a variety of ways. One way is to treat the plasmid with an appropriate restriction enzyme and analyze the resulting fragments for the presence of the foreign gene. Other techniques have been indicated above.

Once the recombinant plasmid has been replicated in *E. coli* and isolated, the *E. coli* may be grown and multiplied and the recombinant plasmid employed for transformation of the *S. cerevisiae* strain.

The term GAL1 promoter as employed in the present invention, also designated $P_{GAL_1}$, is preferably either a 0.755 or 0.82 kilobase DNA sequence from the yeast genome which contains signals for transcription of the GAL1 gene into mRNA and subsequent translation of the mRNA. The coding sequence for galactokinase is not present in this DNA fragment, but the fragment can direct the expression of foreign genes and the regulation follows the mode for the GAL1 gene. [See St. John, T. P. and Davis, R. W., *J. Mol. Biol.* 152, 285-315 (1981).]

The bovine growth hormone gene referred to, which can be promoted by the promoter used in this invention, is a protein of about 22,000 daltons synthesized in anterior pituitaries. The hormone is required for pre-adult growth. Bovine growth hormone (BGH) contains a single polypeptide of 191 amino acids with two disulfide bridges synthesized initially as a pre-growth hormone containing an amino-terminal extension of 26 amino acid residues. [See Miller, W. L., Martial, J. A. and Baxter, J. D., *J. Biol. Chem.* 255, 7521-7524 (1980); Keshet, E., Rosner, A., Bernstein, Y., Gorecki, M. and Aviv, H., *Nucleic Acids Res.* 9, 19-30 (1980); and Lingappa, V. R., Deviller-Thiery, A. and Blobel, G., *Proc. Nat. Acad. Sci. USA* 74, 2432-2436 (1977).]

The interferon gene referred to, which can be promoted by the promoter used in this invention, is any one of the three classes of interferon genes described below:
(a) leukocyte—derived from leukocyte or lymphoblastoid cells, designated LeIFN or IFN-α;
(b) fibroblast—derived from fibroblast cells, designated FIFN or IFN-β; and (c) immune—derived from mitogen- or antigen-stimulated lymphoid cells, designated IFN-γ.

Such interferon genes are described in:

Goeddel, D. V., Leung, D. W., Drell, T. J., Gross, M., Lawn, R. M., McCandliss, R., Seeburg, P. H., Ullrich, A., Yelverton, E., and Gray, P. W., *Nature* 290, 20-26 (1981).

Allen, G. and Fantes, K. H., *Nature* 287, 408–411 (1980) and preceding reference.

Zoon, K. C., *Science* 207, 527–528 (1980).

Mantei, N., Schwartzstein, M., Streuli, M., Panam, S., Nagata, S., and Weissman, C., *Gene* 10, 1–10 (1980).

Streuli, M., Nagata, S., and Weissman, C., *Science* 209, 1343–1347 (1980).

Preferably in the methods of this invention pre-pro-rennin and prorennin can each be obtained by isolation of pre-prorennin DNA material. The pre-prorennin is a precursor of prorennin. By removing portions of the pre-prorennin DNA, one could obtain genetic material which will code for prorennin.

Pre-prorennin or prorennin genes in accordance with this invention comprise any nucleotide sequences coding for the amino acid sequence of pre-prorennin or prorennin respectively and exclude any intervening nucleotide sequences present in the genomic DNA encoding pre-prorennin or prorennin respectively. These genes are also provided attached to vectors which replicate in suitable host cells.

For the purposes of this application, the prorennin gene is defined as any sequence of nucleotides which codes for the prorennin molecule, the amino acid sequence of which is described in the literature (B. Foltmann, V. B. Pedersen, H. Jacobsen, D. Kauffman, and G. Wybrandt, *Proc. Nat. Acad. Sci. USA* 74, 2321–2324 [1977]).

The pre-prorennin gene includes the sequence of nucleotides coding for prorennin, but also includes 48 additional nucleotides on the 5' end which code for the amino-terminal precursor polypeptide found on the pre-prorennin enzyme.

The yeast strain employed as the host cell in the preferred embodiment of the present invention is *Saccharomyces cerevisiae*, a common laboratory strain of yeast used for its low toxicity and well-known genetic characteristics. This strain is readily cultivatable on a large scale. However, the recombinant DNA material of the present invention containing a GAL1 promoter can be used to express a polypeptide product in any yeast cells capable of transformation, including yeast mutants that alter regulation.

*Saccharomyces cerevisiae* is a yeast whose vegetative reproduction occurs by multilateral budding cells. Such cells are usually found in pairs or small clusters. The species is usually diploid where spores are produced directly in vegetative cells, but the species can also be grown in higher ploidy. In addition, *S. cerevisiae* forms an ascus with one to four spheroidal spores in each ascus. The ascus for this species does not rupture at maturity. The yeast has a strongly fermentative as well as respiratory metabolism. Selected strains are referred to as distillers' yeasts and baker's yeast.

The vast majority of yeasts can be cultivated under relatively uniform conditions on common laboratory media. The usual growth requirements of yeast include:
(a) organic carbon compound for carbon and energy;
(b) organic or inorganic nitrogen for the synthesis of proteins and nucleic acids;
(c) various minerals (including compounds furnishing trace elements); and
(d) frequently a mixture of vitamins.

Such growth requirements are met by yeast nitrogen base (YNB, obtained from Difco), a chemically defined medium which contains a number of trace elements, 9 vitamins, trace amounts of amino acids to stimulate growth of certain fastidious yeasts and the principal minerals, potassium phosphate, magnesium sulfate, sodium chloride, and calcium chloride. The nitrogen source is ammonium sulfate. The desired carbon source must be added and is normally at a concentration of 0.5–3%. Additions are made to this medium to fit particular strain requirements. The pH range of the medium is usually from pH 3–8. The preferred range is pH 4.5–6.5.

The starting point for obtaining the cells of the present invention is the use of recombinant DNA techniques known in the art to obtain the genetic material desired and to insert it into the host cell after which the host cell is cloned Preferably, the gene which one wishes to ultimately clone in yeast is isolated in a first step by obtaining messenger RNA of the gene from a primary source. In the case of BGH, this is obtained by isolation from the bovine pituitaries. The messenger RNA can be isolated as by the method of Deeley, et al. (R. G. Deeley, J. I. Gordon, A. T. H. Burns, K. P. Mullinix, M. Bina-Stein, R. F. Goldberger *J. Biol. Chem.* 252 8310-8319 [1977]) and poly A-enriched RNA can be obtained by chromatography over oligo (dT) cellulose by the method of R. C. Desrosiers, K. H. Friderici, & F. M. Rottman *Biochemistry* 14 4367–4374 (1975).

The messenger RNA is then converted to double-stranded DNA by conventional means First, the complimentary copy of the DNA is made from the messenger RNA by conventional recombinant DNA means as by the use of AMV reverse transcriptase. For example, the methods of A. Efstratiadis, F. C. Kafatos, A. M. Maxam and T. Maniatis, *Cell* 7 279-288 (1976), R. Higuchi, G. V. Paddock, R. Wall and W. Salser, *Proc. Nat. Acad Sci. USA* 73, 3146–3150 (1976), D. L. Kacian and J. C. Myers, *Proc. Nat. Acad Sci. USA* 73, 2191–2195 (1976), M. P. Wickens, G. N. Buell and R. T. Schimke, *J. Biol Chem* 253, 2483–2495 (1978), G. M. Wahl, R. A. Padgett and G. R. Stack, *J. Biol. Chem.*, 254, 8679–8689 (1979) can be used to obtain the copy DNA (cDNA). The RNA portion can be disposed of by breaking the strands as known in the art using any of the above methods or by heat denaturing according to the method of Wickens, et al. (1978).

Next, enzymes such as *E. coli* DNA polymerase I or AMV reverse transcriptase can be used to turn the cDNA into double-stranded DNA using the methods of the publications above and J. I. Gordon, A. T. H. Burns, J. L. Christmann & R. G. Deeley, *J. Biol. Chem.* 253, 8629–8639 (1978).

Thirdly, synthetic linkers can be attached to both ends of the double-stranded DNA as for example by the use of HindIII or EcoRI synthetic oligonucleotide linkers using conventional methods such as described in R. H. Scheller, T. L. Thomas, A. S. Lee, W. H. Klein, W. D. Niles, R. J. Britten and E. H. Davidson, *Science* 196, 197-200 (1977), T. H. Fraser and B. J. Bruce, *Proc. Natl. Acad. Sci. USA* 75 5936–5940 (1978), A. Ullrich, J. Shine, J. Chirgwin, R. Pictet, E. Tischer, W. J. Rutter & H. M. Goodman, *Science* 196, 1313–1319 (1977), J. Shine, P. H. Seeburg, J. A. Martial, J. D. Baxter & H.

M. Goodman, *Nature* 270, 494-499 (1977), or P. H. Seeburg, J. Shine, J. A. Martial, J. D. Baxter & H. M. Goodman, *Nature* 270, 486-494 (1977).

In a fourth step, the DNA molecule is integrated into the chromosome or attached to a vector which can be a plasmid, virus or cosmid as known in the art. Such vectors include:

pBR322 (F. Bolivar, R. L. Rodriguez, P. J. Greene, M. C. Betlach, H. L. Heyneker, H. W. Boyer, J. H. Crosa, S. Falkow, 1977 *Gene* 2 95-119)

pMB9 (R. L. Rodriguez, F. Bolivara, H. M. Goodman, H. W. Boyer, M. C. Betlach in "Molecular Mechanisms in the Control of Gene Expression" [D. P. Nierlich, W. J. Rutter, C. F. Fox, Eds.]471 Academic Press New York 1976)

pSC101 (S. N. Cohen, A. C. Y. Chang, H. W. Boyer, R. B. Helling 1973 *Proc. Nat. Acad. Sci. USA* 70 3240)

λ gtWES (D. Tiemeier, L. Enquist, P. Leder *Nature* 263-527) (1976)

λ charon phages (F. R. Blattner, et al *Science* 196 161-169) (1977)

fl R229 (J. D. Boeke *Molec. Gen. Genetics* 181, 288-291) (1981)

pJC75-58 (J. Collins *Methods in Enzymology* 68 309-326) (1979)

This step is again carried out outside of the final host cell. Useful techniques for this procedure are described in the references above in connection with the linkers as well as in the following publications: V. Hershfield, H. W. Boyer, C. Yanofsky, M. A. Lovett & P. R. Helinski, *Proc. Natl. Acad. Sci. USA* 71, 3455-3459 (1974), N. E. Murray & K. Murray, *Nature* 251, 476-482 (1974), F. R. Blattner et al, *Science* 196, 161-169 (1977).

In a fifth step, the recombinant DNA molecule can be introduced into the cytoplasm of the host cell line using conventional procedures such as described in M. Mandel & A. Higa (1970) *J. Mol. Biol.* 53 159-162, P. C. Wensink, D. J. Finnegan, J. E. Donelson & D. S. Hogness, *Cell* 3, 315-325 (1974), S. N. Cohen, A. C. Y. Chang and L. Hsu, *Proc. Natl. Acad. Sci. USA* 69, 2110-2114 (1972), H. M. Goodman, and R. J. MacDonald, *Methods in Enzymology* 68, 75-90 (1979), E. M. Lederberg and S. N. Cohen, *J. Bact.* 119, 1072-1074 (1974).

Recognition of the correct clone may be accomplished by the method of hybridization selection or by probing with synthetic oligonucleotides, (T. Taniguchi, Y. Fujii, Kuriyama and M. Muramatsu, *Proc. Natl. Acad. Sci. USA* 77, 4003-4006 (1980), R. P. Ricciardi, J. S. Miller & B. E. Roberts, *Proc. Natl. Acad. Sci. USA* 76, 4927-4931 (1979), D. L. Montgomery, B.D. Hall, S. Gillam and M. Smith, *Cell* 14, 673-680 [1978]).

The newly modified host cell is then cloned and expression of the material desired obtained. For example, the technique of Guarente, et al. using the lactose operon promoter, (1980) (L. Guarente, G. Lauer, T. M. Roberts & M. Ptashne, *Cell* 20, 543-553 [1980], L. Guarente, T. M. Roberts & M. Ptashne, *Science* 209, 1428-1430 [1980]) allows one to obtain and optimize expression of foreign DNA.

Figure 3:
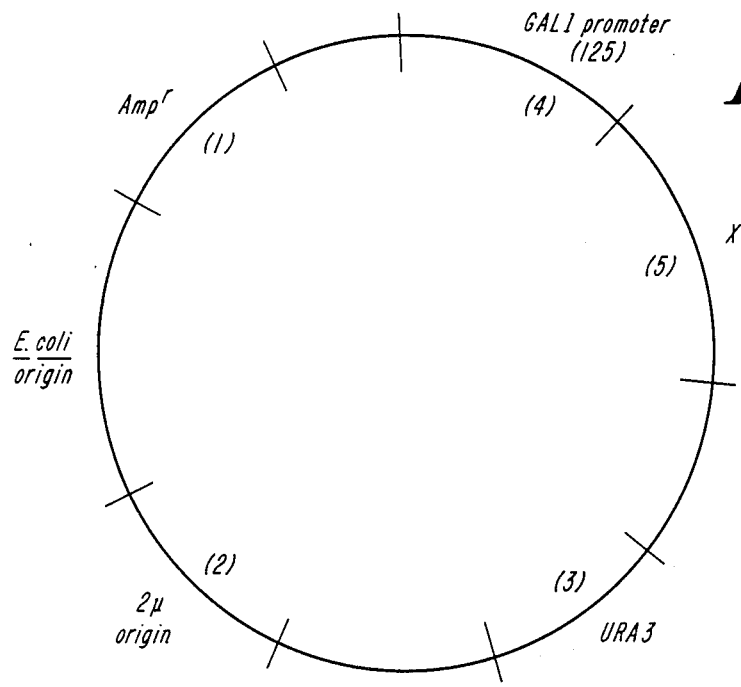

In the present invention, the arrangement of the DNA segments in the plasmid construction is shown diagramatically in FIG. 3.

Figure 2:
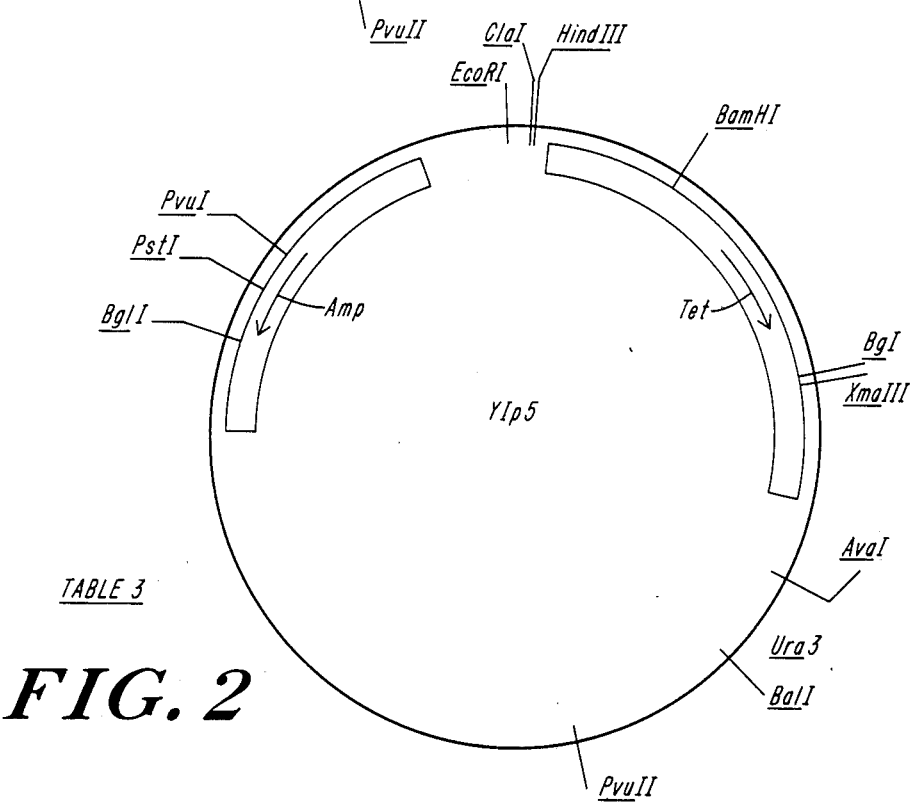

This construction consists of several components generally used in "shuttle" vectors, i.e., plasmids that can be maintained either in *E. coli* or yeast. The plasmid described in FIG. 3 is a modified construction of plasmid YIp5, as described by K. Struhl, D. T. Stinchcomb, S. Scherer and R. W. Davis, *Proc. Nat. Acad. Sci. USA* 76, 1035-1039 (1979) [see FIG. 2]. Segment (1) is a 2.4 kilobase fragment of plasmid pBR322 and contains a DNA replication origin and β-lactamase gene, allowing propagation of the DNA in *E. coli* and continuous selection for its presence by ampicillin resistance. Segment (2) is a 1.6 kilobase HpaI to HindIII fragment of the yeast 2μ plasmid containing an initiation site for replication in yeast. [The 2μ plasmid is described by J. L. Hartley and J. E. Donelson, *Nature* 286, 860-865 (1980)]. Segment (3) is the URA3 gene from the yeast genome (1.1 kb long) to allow the selection of yeast harboring the plasmid by virtue of its complementation of the ura3⁻ mutation in the host strain. [The URA3 gene is described by M. Bach, F. Lacroute and D. Botstein, *Proc. Nat. Acad. Sci. USA* 76,386-390 (1979)

Segment (4) is a 0.755 or 0.82 kb fragment of DNA from the yeast genome which contains signals for transcription of the GAL1 gene into mRNA and subsequent translation of the mRNA. The GAL1 gene is repressed when the yeast strain is grown in high glucose medium. The coding sequence for galactokinase is not present in the 0.755 or 0.82 kb fragments. These pieces of DNA can direct the expression of foreign genes and the regulation follows the mode for the GAL1 gene as herein disclosed.

Segment (5) is a fragment of DNA which encodes for the desired polypeptide product sequence. This piece of DNA is oriented so that transcription of the mRNA is controlled by a GAL1 promoter. The sequence coding for the signal peptide was removed and an ATG translational initiation codon was incorporated. Therefore, a gene initiated by methionine is used for the studies.

The plasmid was constructed by ligation of DNA pieces from various sources and synthetic linkers. The sequence at the junction of the 0.82 kb GAL1 promoter and the foreign gene sequence is:

(I)

where X is the foreign gene. The sequence TCGACC is part of a synthetic SalI linker and CCCCGGATC is part of a BamHl linker.

The sequence at the junction of the 0.755 kb GAL1 promoter and the foreign gene sequence is:

where X is the foreign gene.

The plasmid was first cloned and amplified in *E. coli* and then transformed into yeast. Expression levels were determined for various genes using similar constructions. In the case of BGH, for example, a fusion gene of BGH' 'lacZ replaced the BGH gene (at X) in FIG. 3. This construction contains essentially the whole BGH sequence (only the coding sequence for 4 amino acids for the N-terminus is missing) and nearly the whole lacZ gene. By monitoring the β-galactosidase (lacZ gene product) activity, approximately 80,000 molecules of fusion protein were produced per cell in strain CGY 150 (αleu2-3 ura3-52 GAL+).

Permissible modifications in the production of a polypeptide product in yeast would include:
Different terminators can be used.

With respect to BGH, the N-terminal amino acid is heterologous for BGH with both phenylalanine (Phe) and alanine (Ala) being observed. This heterogeneity is a consequence of ambiguous processing of the precursor molecule (pre-growth hormone). The gene described above codes for the Phe-BGH. The other gene for Ala-BGH can also be used for expression.

Mutations in the GAL1 promoter (element (4) in Table 4) can affect the level of expression or the mode of regulation. Other mutations in the chromosomal genome may also have the same effects. In fact, there are mutants available to turn a GAL1 promoter on constitutively. These strains can be used to get higher levels of expression.

The DNA segment containing $P_{GAL1}$ linked to the foreign gene (elements (4) and (5) in Table 4) can be integrated into the yeast chromosome for a stable construction rather than having this segment on an extrachromosomal plasmid.

The ATG initiation codon in the foreign gene can be replaced by other sequences such as sequences coding for a signal peptide. Further, the protein could be secreted from yeast cells into the medium.

Different lengths and sequences of DNA can be used at the junction of the GAL1 promoter and the foreign gene sequence to optimize the level of production. For instance, sequence (I) could be changed to:

Other sequences in this region can be derived by performing mutagenesis.

Different lengths of the GAL1 promoter can be used. A terminator for transcription from the yeast genome can be added to the C-terminus of the BGH gene.

The term GAL1 promoter, as used herein, includes any portion of a 0.755 or 0.82 kilobase DNA sequence which acts to cause expression of galactokinase in yeast.

The yeast strain described herein will produce the desired polypeptide product if the medium contains galactose. The medium should contain 6.7 g/l yeast nitrogen base, 2% galactose and the appropriate amino acids. If the polypeptide product proves to be deleterious to the host strain, the production can be repressed by growing the yeast in a medium containing 2% glucose, 6.7 g/l yeast nitrogen base and then inducing the production of the polypeptide product after growth has ceased by transferring the yeast to the galactose medium. The cells are centrifuged and the cell-free extract is obtained by breaking cells by vigorous vortexing with glass beads.

EXAMPLE 1

Production of Bovine Growth Hormone

1. Isolation of BGH mRNA

Bovine pituitaries were collected shortly after killing and were frozen immediately on dry ice. 14.4 grams of tissue were disrupted by means of a Waring blender into 200 ml of cold buffer (10° C.) consisting of 50 mM Tris-HCl, pH 7.5, 8 M guanidine HCl, and 1 mM dithiothreitol. The resulting solution was centrifuged at 5° C. in a Sorval SA600 rotor at 10,000 rpm for 17 minutes. The material was resuspended by homogenization and sat on ice for one hour in 40 ml of cold buffer consisting of 20 mM NaOAc, 20 mM EDTA, and then treated with half volume of ice-cold absolute ethanol. After 1 hour at −b 20°0 C., the precipitate was pelleted by a centrifugation at 3,000 rpm for 30 minutes at −10° C. The pellet was resuspended two times in 20 ml of the preceding buffer, treated with half volume of ice cold absolute ethanol, incubated one hour at −20° C. and the pellet collected as decribed previously. The final pellet was resuspended in 8 ml of 0.1M EDTA with heating at 60° C., and then 0.1 volume of 2M NaOAC, pH 5.0, and 2 volumes of ice-cold absolute ethanol were added and the solution placed at −20° overnight. The RNA precipitate was collected by centrifugation at 8,000 rpm for 20 minutes at −10° C., and was dissolved in 5 ml water. The yield was 5 mg RNA. The RNA solution was diluted with 5 ml of 2× concentrated binding buffer (20 mM Tris-HCl, pH 7.5; 2mM EDTA, pH 7.0; 0.4% SDS; and 0.24 M NaCl). The RNA was applied to a 1.5 ml oligo-dT-cellulose column, the column was washed with 1x concentrated binding buffer and then the poly A-containing RNA (mRNA) was eluted by washing the column with binding buffer containing no NaCl. About 100 mg of poly A-containing RNA were obtained. A portion of the poly A-containing RNA was translated in vitro in a rabbit reticulocyte lysate system [Pelham, H. R. B. and Jackson, R. J., *Eur. J. Biochem.* 67 247-256 (1976)] to confirm the isolation of mRNA coding for BGH.

2. Preparation of double-stranded copy DNA (cDNA)

About 2.5μg of cDNA was synthesized from 25μg of the poly A-containing RNA by incubation for one hour at 42° C. in 50 mM Tris-HCl, pH 8.3; 100 mM KCl; 8mM MgCl$_2$; 0.4 mM dithiothreitol; 5 mM each dATP, dGTP and dTTP; and 20μg/ml oligo $(-dT)_{12-18}$, containing 100 units reverse transcriptase and 1.3μCi α-$^{32}$P-dCTP(1.8 Ci/mmole). After heating the reaction mixture at 100° C. for 3.5 minutes, quick chilling on ice for approximately 3 minutes and removing the precipitated protein by centrifugation, to the supernatant was added HEPES-NaOH, pH 6.9, to 100 mM; MgCl$_2$ to 5 mM; dithiothreitol to 0.5 mM; and deoxynucleoside triphosphates to 0.125 mM. Incubation of this mixture with 300 units of *E. coli* DNA polymerase I for 2.5 hours at 15° C. produced 1.8μg of double-stranded cDNA. The DNA was phenol extracted, separated from unincorporated triphosphates by chromatography on Sephadex G-100 (13.5 ml column, 0.7 cm×35 cm, eluted with 20 mM NaCl) and ethanol precipitated overnight at −20° C. by addition of 1/10 volume 2 M NaOAc, pH 5, and 2.5 volumes cold ethanol. The double-stranded cDNA was then treated with 8,000 units of S1 nuclease at 37° C. for one hour in buffer (0.3 M NaCl, 30 mM NaOAc, pH 4.6, 3 mM ZnSO$_4$). The reaction was terminated by addition of EDTA to 10 mM, and Tris-HCl, pH 8.3, to 200 mM, and the mixture applied to a Biogel A-150m column (0.75 cm×40 cm) equilibrated and eluted with 10 mM Tris-HCl, pH 7.5, 250 mM NaCl and 1 mM EDTA. The peak fractions (0.5 ml each) of large molecular weight DNA were pooled and ethanol precipitated by addition of 1/10 volume 2 M NaOAC, pH 5, and 2.5 volumes cold absolute ethanol.

3. Addition of EcoRI Linkers

The S1-treated double-stranded cDNA (0.21μg) was incubated in buffer (60 mM Tris-HCl, pH 7.5; 8 mM MgCl; 5 mM dithiothreitol, 1 mM ATP and 5 mM of each deoxynucleoside triphosphate) with 9 units of *E. coli* DNA polymerase I at 10° C. for 10 minutes and then placed on ice. This blunt-ended double stranded cDNA was next incubated in 65 mM Tris-HCl, pH 7.5; 6 mM Mg Cl$_2$; 5 mM dithiothreitol; 1 mM ATP, with 160 pmoles of $^{32}$P-labelled EcoRI synthetic linker (100x excess over cDNA ends) and 4 blunt-end units of T4 DNA ligase at 15° C. for 5 hours, cooled on ice, treated with EcoRI restriction endonuclease (New England Biolabs, 9 units) in 100 mM Tris-HCl, pH 7.5, 50 mM NaCl, 5.6 mM MgCl$_2$ at 37° C. for 4 hours 45 minutes and then phenol extracted. The reaction was fractionated on a Biogel A-150m column (0.7 cm x 31.5 cm). Fractions (0.5 ml each) containing high molecular weight DNA were pooled and ethanol precipitated.

This double stranded cDNA with EcoRI cohesive termini was then ligated to fl phage CGF4 double-stranded DNA which had been cut open with EcoRI restriction endonuclease and treated with calf intestinal alkaline phosphatase by the method of H. Goodman and R. J. MacDonald [Goodman, H. M. and MacDonald, R. J., *Methods in Enzymol.* 68, 75–91 (1979)]to remove the terminal phosphates. The ligation reaction contained 60 mM Tris-HCl, pH 7.5; 6 mM MgCl$_2$; 7 mM dithiothreitol; 0.12µg double-stranded cDNA; 1.2µg CGF4 DNA; 0.5 mM ATP and 450 cohesive end units of T4 DNA ligase. Ligation was for 19 hours at 15° C.

4. Transfection of *E. coli* DB4548 with recombinant CGF4 DNA

*E. coli* strain CGE6 (DB4548; hsdR$^-$, hsdM$^+$, sup E, sup F, Bl$^-$, met$^-$) was grown in 150 ml tryptone broth at 37° C. with shaking and harvested at OD$_{700}$=0.5 by centrifugation at 7,000 rpm for 10 minutes at 4° C. The cells were resuspended in 70 ml ice cold 50 mM CaCl$_2$ and allowed to sit at 0° C. for 30 minutes. The suspension was then centrifuged at 7,000 rpm for 10 minutes at 4° C. and resuspended in 3 ml ice cold 50 mM CaCl$_2$. After standing at 0° C. for 2 hours the cells were used for transfection. Either 1µl or 2 µl of 1:40 dilution of ligation reaction in 50 mM Tris-HCl, pH 7.5, was added to each of 12 tubes containing 50 ml sterile 50 mM Tris-HCl, pH 7.5. One-tenth milliliter of the CaCl$_2$-treated cells was added to each tube and the mixtures set on ice for 30 minutes. After warming to 37° C. for 2 minutes, 0.2 ml of CGE5 (JM101: J. Messing (1979), F'traD36 proAB lacIZVM15 in a $\nabla$ (lac pro) SupE thi$^-$ background) overnight culture and 3 ml of 0.7% soft agar were added, and the mixture poured into tryptone agar plates. Incubation at 37° C. overnight produced over 3000 plaques.

5. Identification of a recombinant-CGF4 carrying the bovine growth hormone sequence The plaques were transferred to ritrocellulose and probed as described by Benton and Davis [Benton, W. D. and Davis, R. W., *Science* 196, 180–182 (1977]using a $^{32}$P-labelled BGH cDNA. The phages which hybridize intensely to the cDNA probe were picked from the plates and stored in TY medium at 4° C. Samples of the intact phage were amplified by growth overnight on CGE5 cells, harvested by centrifugation, and subjected to electrophoresis in a 0.6% agarose gel containing 0.37 M Tris-glycine, pH 9.5, and stained with ethidium bromide after treatment in 0.2 N NaOH for one hour and neutralization in 0.5 M Tris-HCl, pH 7.4. The migration is inversely proportional to the log of the size of the phage DNA and allowed selection of about 45 phages carrying inserted BGH DNA of size of 600 to 1200 base pairs. Single stranded DNA was prepared by the method of Horiuchi, et al. [Horiuchi, K., Vovis, G. F. and Zinder, N. D., *J. Biol. Chem.* 249, 543–552 (1974)]and hybrid selection was carried out. The eluted RNA was translated in a reticulocyte lysate system by the method of Pelham and Jackson [Pelham, H. R. D. and Jackson, R. J., *Eur. J. Biochem.* 67, 247–256] and analysis of the protein products revealed the production of authentic immunoprecipitable BGH. Double-stranded RFI DNA was prepared from the phages by the method of Moses, et al. [Moses, P. B., Boeke, J. D., Horiuchi, K. and Zinder, N. D., *Virology* 104, 267–273 (1980)]. Each DNA was cut with EcoRI and PstI restriction endonucleases and the resulting fragments analyzed on an agarose gel to confirm that the insert contained a PstI site. One of the phage DNA's which had a segment of about 350 base pairs (bp) was chosen for further study. The DNA insert was sequenced by the method of Maxam and Gilbert [Maxam, A. M. and Gilbert, W., *Methods in Enzymol.* 68, 499–560 (1980)]as shown in Table 2.

TABLE 2

```
          -110  EcoRI
GAATTCCGGGTCCTGTGGACAGCTCACCAGCT
                                                         -26
                                MET met ala ala gly pro arg thr ser leu leu ala phe ala leu
                                ATG ATG GCT GCA GGC CCC CGG ACC TCC CTG CTC CTG GCT TTC GCC CTG
                                                         PatI
     -20                                                                                      -1 1
leu cys leu pro trp thr gln val val gly ala phe pro ala met ser leu ser gly leu phe ala asn ala val leu arg ala gln his
CTG TGC CTG CCC TGG ACT CAG GTG GTG GGC GCC TTC CCA GCC ATG TCC TTG TCC GGC CTG TTT GCC AAC GCT GTG CTC CGG GCT CAG CAC
 -+                              HaeII(HhaI)                                                                         20
                                                                                                                     60

-10                                     10
leu his gln leu ala ala asp thr phe lys glu phe glu arg thr tyr ile pro glu gly gln arg tyr ser ile gln asn thr gln val
CTG CAT CAG CTG GCT GCT GAC ACC TTC AAA GAG TTT GAG CGG ACC TAC ATC CCG GAG GGA CAG AGA TAC TCC ATC CAG AAC ACC CAG GTT
         PvuII                          (HhaI)                                                                       50
                                                                                                                     150 ala phe cys phe ser glu thr ile pro ala pro thr gly lys asn glu ala gln gln lys ser asp leu glu leu leu arg ile ser leu
GCC TTC TGC TTC TCT GAA ACC ATC CCG GCC CCC ACG GGC AAG AAT GAG GCC CAG CAG AAA TCA GAC TTG GAG CTG CTT CGC ATC TCA CTG
                                                                                                     80
                                                                                                     240

90                                                     100                                           110
leu leu ile gln ser trp leu gly pro leu gln phe leu ser arg val phe thr asn ser leu val phe gly thr ser asp arg val tyr
CTC CTG ATC CAG TCG TGG CTT GGG CCC CTG CAG TTC CTC AGC AGA GTC TTC ACC AAC AGC TTG GTG TTT GGC ACC TCG GAC CGT GTC TAT
                             ApaI                 PstI                                                              330

120                                                     130                                      140
glu lys leu lys asp leu glu glu gly ile gln ala leu met arg glu leu glu asp gly thr pro arg ala gly gln ile leu lys gln
GAG AAG CTG AAG GAC CTG GAG GAA GGA ATC CAG GCC CTG ATG CGG GAG CTG GAA GAT GGT ACC CCC CGG GCT GGG CAG ATC CTC AAG CAG
                                                                                          SmaI                      420

150                                                     160                                     170
thr tyr asp lys phe asp thr asn met arg ser asp asp ala leu leu lys asn tyr gly leu leu ser cys phe arg lys asp leu his
ACC TAT GAC AAA TTT GAC ACA AAC ATG AGG AGT GAC GAC GCG CTG CTC AAG AAC TAC GGT CTG CTC TCC TGC TTC CGG AAG GAC CTG CAT
                                                                                                                    510

180                                              190
lys thr glu thr tyr leu arg val met lys cys arg arg phe gly glu ala ser cys ala phe END
AAG ACG GAG ACG TAC CTG AGG GTC ATG AAG TGC CGC CGC TTC GGG GAG GCC AGC TGT GCC TTC TAG
                                                             PvuII TTGCCAGCCATCTGTTGTTTGCCCCTCCCCCGTGCCTTCCTTGACCCGGTGCCACTCCCACTGTCCTTCCTAATAAAATGAGGAAATTGCATGC(A)n
                                          607                                                    677
```

6. Expression of BGH in *Saccharomyces cerevisiae*

Figure 4:
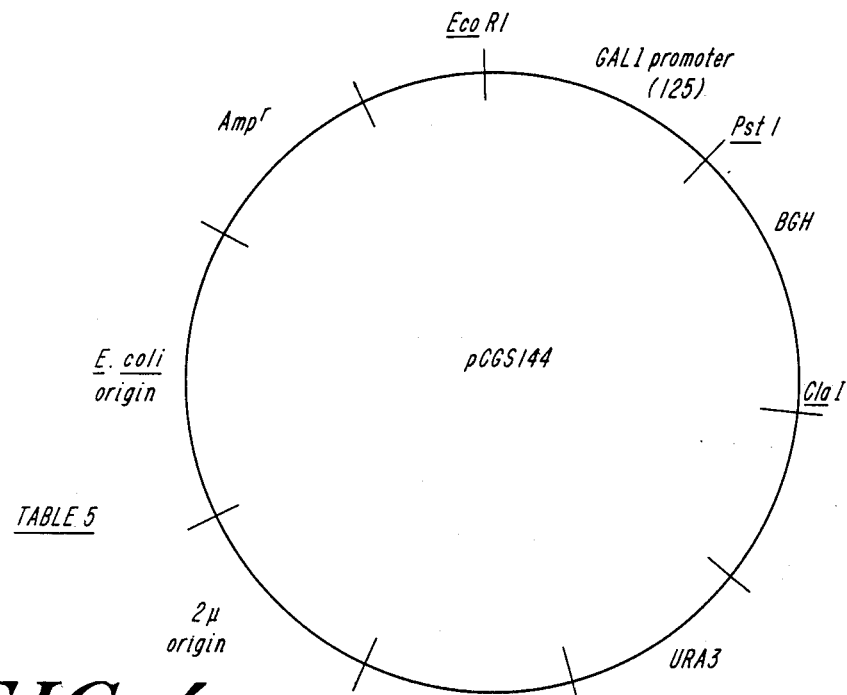

A plasmid, pCGS144, as seen in FIG. 4, designed to facilitate obtaining expression of BGH in yeast was constructed. In order to produce the BGH in yeast, an ATG initiation codon was incorporated at the 5'-side of the first amino acid (phenylalanine). Based on the fact that HaeII cuts at the 3'-side of the first codon, a HaeII digest was carried out to open the 5'-end at the Phe codon. The cohesive ends were trimmed back by treating the DNA with 4 units *E. coli* DNA polymerase I (Klenow fragment) in the presence of 0.5 mM dATP in 6.6 mM Tris-HCl, pH 7.5; 6.6 mM NaCl; 6.6 mM MgCl$_2$ and 66 mM dithiothreitol, for 30 minutes at room temperature, and then blunt-ended with S1 nuclease.

A ClaI synthetic linker (CATCGATG) containing the ATG initiation codon was ligated onto the blunt-ended fragment in 66 mM Tris-HCl, pH 7.5; 10 mM MgCl$_2$; 10 mM 2-mercaptoethanol; 1 mM ATP with 500 pmole $^{32}$P-ClaI linker; 4 pmoles DNA (20 μg) and 4 blunt-end units of T4 DNA ligase at 17° C. overnight. This ligation created an ATG initiation codon and restored the first codon TGT. ClaI polylinker was removed by treating the fragment with 20 units restriction endonuclease ClaI for 3 hours at 37° C. in a 20 μl reaction containing 10 mM Tris-HCl, pH 7.5; 10 mM MgCl$_2$; and 0.1 mg/ml bovine serum albumin. The resulting fragment was cloned into the ClaI site of plasmid pBR322. The plasmid (10 μg) was cut with the restriction endonuclease ClaI (New England Biolabs, 20 units) for 2 hours at 37° C. in a 20 μl reaction containing 10 mM Tris-HCl, pH 7.5; 10 mM MgCl$_2$ and 0.1 mg/ml bovine serum albumin. The preparation of restriction cut plasmid was phenol extracted, ethanol precipitated and treated with calf intestinal phosphatase by the method of H. Goodman and R. J. MacDonald [Goodman, H. M. and MacDonald, R. J., *Methods in Enzymology* 68, 75–91 (1979)] to remove the terminal phosphates. Approximately 0.5 pmole of the ClaI fragment and 0.3 pmole of the ClaI cut plasmid were ligated together at 15° C. for 3 hours in a 20 μl reaction containing 66 mM Tris-HCl, pH 7.5; 6 mM MgCl$_2$; 10 mM dithiothreitol; 1mM ATP; and T4 DNA ligase (New England Biolabs, 300 units) creating plasmid pCGE27.

Transformation-competent *E. coli* strain CGE43 (LG90; F$^-$ $\triangledown$(lacro/ )X111) was prepared as described previously for CGE6, and 5 μl of the ligated DNA was mixed with 200 μl of the cells for 30 minutes at 0° C., heat treated at 37° C. for 2 minutes, incubated at room temperature for 10 minutes, and diluted five-fold with fresh tryptone broth. After incubation for 30 minutes at 37° C. with shaking, cells were plated on tryptone plates containing ampicillin (20 μg/ml). Ampicillin-resistant colonies were picked, and the plasmid DNA was prepared and analyzed by restriction enzyme digestion. By these criteria several cells carried the desired plasmid, pCGE27. Plasmid pCGE27 DNA (10 μg) was cut with the restriction endonuclease HindIII (Collaborative Research, Inc., 12 units) for 2 hours at 37° C. in a 20 μl reaction containing 10 mM Tris-HCl, pH 7.5; 10 mM MgCl$_2$; 60 mM NaCl; and 0.1 mg/ml bovine serum albumin). This DNA was next digested with the endonuclease EcoRI (Collaborative Research, Inc., 15 units) for 3 hours at 37° C. in a 20 μl reaction containing 100 mM Tris-HCl, pH 7.6; 10 mM MgCl$_2$; 50 mM NaCl; and 1 mg/ml bovine serum albumin. The restriction cut DNA was trimmed back with *E. coli* DNA polymerase I (Klenow fragment) in the presence of 0.5 mM dTTP and made blunt-ended with S1 nuclease as described previously. The DNA was then phenol extracted, ethanol precipitated, redissolved in water and applied to a preparative horizontal 1.5% agarose gel. After electrophoresis for 2 to 3 hours in 40 mM Tris-acetate, pH 7.2, the gel was stained with ethidium bromide and examined under long wavelength ultraviolet light. The digested DNA was extracted by freezing and thawing the gel pieces [Thuring, et al., *Anal. Biochem* 66, 213 (1975)]. The DNA fragment was ethanol-precipitated and redissolved in water. A plasmid (pGL101; 20 μg) containing 95 base pairs of P$_{lac}$ inserted at EcoRI/PvuII site of pBR322 was cut with the restriction endonuclease PvuII (New England Biolabs, 24 units) for 6 minutes at 37° C. The restriction cut DNA was phenol extracted, ethanol precipitated, and redissolved in water. This PvuII opened vector was analyzed by gel electrophoresis and excised from the gel (see above). Approximately 0.25 pmole of the DNA fragment coding for BGH was ligated into plasmid pGL101 opened at its PvuII site (see above) for 4 hours at 14° C. in a 20 μl reaction containing 66 mM Tris-HCl, pH 7.6; 6.6 mM MgCl$_2$; 10 mM dithiothreitol; 1 mM ATP and T4 DNA ligase (New England Biolabs, 300 units). Transformation-competent *E. coli* strain CGE43 cells were prepared exactly as described above, and 5 μl of the ligated DNA was mixed with 100 μl of the cells for 30 minutes at 0° C., heat treated at 37° C. for 2.5 minutes, and diluted ten-fold with fresh tryptone broth. After incubation for 30 minutes at 37° C. with shaking, cells were plated on tryptone plates containing ampicillin (20 μg/ml). Ampicillin-resistant colonies were picked, and the plasmid DNA was prepared and analyzed by restriction enzyme digestion for the correct orientation. By these criteria several strains carried the desired plasmid, pCGE22, which contained the P$_{LAC}$-Phe-BGH gene.

The fragment containing the gene for BGH was isolated from plasmid pCGE22 (30 μg) by partial cutting the plasmid with restricton endonuclease PvuII and PstI at 37° C. as above. The restriction cut DNA was phenol extracted, ethanol precipitated, redissolved in water and applied to a preparative 0.5% agarose gel. After electrophoresis in 40 mM Tris-acetate, pH 7.2, the gel was stained with ethidium bromide and examined under long wavelength ultraviolet light. The band was excised and the DNA extracted by freezing and thawing the gel pieces [Thuring, et al., *Anal. Biochem.* 66, 213 (1975)]. The DNA fragment was ethanol precipitated and redissolved in water. Approximately 0.5 pmole of the PvuII/PstI fragment was ligated into plasmid pCGE41 opened at its EcoRI site adjacent to the P$_{LAC}$/'Z region and at PstI site. The EcoRI site was filled in with *E. coli* DNA polymerase I. Ligation was carried out for 2.5 hours at 14° C. in a 20 μl reaction containing 66 mM Tris-Hcl, pH 7.6; 6.6 mM MgCl$_2$; 10 mM dithiothreitol; 1 mM ATP and T4 DNA ligase (Collaborative Research, Inc., 10 units). The ligated DNA was used to transform competent *E. coli* cells which were verified to contain the desired plasmid, pCGE51.

The plasmid, pCGE27, was cut with ClaI restriction enzyme, and the resulting fragment made blunt-ended with S1 nuclease. A SalI synthetic linker (GGTCGACC) was litaged onto the blunt-ended fragment. SalI polylinker was removed by treatment with 20 units restriction endonuclease SalI. It was then cut with PstI. The resulting fragment together with the PstI/XhoI BGH' 'Z fragment of pCGE51 were cloned into the yeast shuttle vector pCGS40 as described previously.

The plasmid, pCGS40, comprises most of pBR322 containing a DNA replication origin and β-lactamase gene for selection in E. coli, with a 1.6 kilobase fragment of the yeast 2μ plasmid containing an initiation site for replication in yeast, with a 1.1 kilobase fragment from the yeast chromosomal DNA carrying a URA3 gene for selection in yeast and with a 0.9 kilobase fragment from yeast chromosomal DNA containing the SUC2 promoter of the yeast invertase gene. The plasmid pCGS40 was constructed by first cutting 60 μg of plasmid pRB118 [Carlson, M. and Botstein, D., Cell 28, 145–154 (1982)] with restriction endonuclease HindIII for 30 minutes at 37° C. and then with restriction endonuclease EcoRI (see above). The restriction cut DNA was phenol extracted, ethanol precipitated, redissolved in water and purified by gel electrophoresis. The digested EcoRI to HindIII 0.9 kilobase band which contains the promoter for the SUC2 gene was excised and the DNA extracted by glass beads. [Vogelstein, B. and Gillespie, D., PNAS 76, 615–619 (1979).] The 0.9 kilobase DNA fragment containing the SUC2 promoter was placed on the plasmid YIp5 (a shuttle vector which can be selected for and maintained in yeast due to the presence of the URA3 gene or E. coli due to the presence of the Ampgene). The resulting plasmid, pCGS46, obtained after ligation and transformation was purified and its structure verified. The plasmid pCGS40 was constructed by cutting the plasmid pCGS46 with restriction endonuclease PvuII for 1 hour at 37° C. A 1.56 kilobase fragment of 2μ DNA from plasmid YEp13, obtained from R. Davis, Stanford University, was removed by cutting YEp13 with HpaI and HindIII. The resulting fragment was gel purified, phenol extracted, ethanol precipitated, and treated with T4 DNA polymerase (see above) in order to create blunt ends at the HindIII restriction cut. After phenol extraction and ethanol precipitation, the PvuII cut DNA and blunt-ended 2μ DNA fragment were purified by gel electrophoresis and ligated together overnight. The resulting plasmid, pCGS40, can be grown and its presence can be selected for in either E. coli or Saccharomyces cerevisiae. Following transformation and restriction analyses, the desired plasmid, pCGS75, was obtained containing BGH' 'Z.

The plasmid, pCGS75, was cut with SalI and then rendered blunt-ended by treatment with E. coli DNA polymerase I. The blunt-ended DNA was then cut with XbaI and the fragment gel purified. This same plasmid was also cut with EcoRI/XbaI to produce a fragment which upon ligation with the previously isolated SalI-blunt-ended/XbaI fragment and an EcoRI/BamHI fragment of pBM125 yielded pCGS118 containing $P_{GAL1}$ BGH' 'Z on a yeast shuttle vector. The $P_{GAL1}$ promoter (820 bp) came from pBM125 (courtesy of R. Davis, Stanford University) which was cut with BamHI, filled in with E. coli DNA polymerase I then cut with EcoRI.

The construction of pCGS144 containing the BGH gene promoted by $P_{GAL1}$ was accomplished by a trimolecular reaction. The GAL1 promoter and part of the BGH gene were removed from pCGS118 by restriction with XbaI and PstI. The rest of BGH was obtained by cutting pCGE27 with PstI and ClaI. These gel purified fragments were ligated with a XbaI/ClaI fragment of pCGS57 which contained part of the 2μ and the URA3 gene.

The yeast strain CGY150 (MATa, leu 2-3, leu 2-112, ura 3-50) was transformed with the BGH plasmid DNA by the method of A. Hinnen, J. B. Hicks, and G. Fink [Hinnen, A., Hicks, J. B. and Fink, G. F., Proc. Nat. Acad. Sci. USA 75, 1929–1933 (1978)]. Yeast transformant CGY196, capable of growth without added uracil due to the presence of URA 3 gene on the plasmid, were picked. (Strain CGY196 bearing plasmid pCGS144 is on deposit with the American Type Culture Collection (ATCC), Accession number 20643, deposited September, 1982.) The yeast cells were grown at 30° C. with agitation in a medium containing 6.7 g/l yeast nitrogen base, 30 mg/l L-leucine and 2% galactose. The synthesis of BGH was induced due to the presence of galactose. After growing to Klett=50 at 30° C. with agitation, the cells were collected by centrifugation, resuspended in 0.25 ml 0.05 M Tris-HCl, pH 7.6, 20% glycerol and 1 mM PMSF, and frozen at −20° C. The cells were disrupted by glass beads by the method of M Rose, et al. [Rose, M., Casadaban, M. J. and Botstein, D., Proc. Nat. Acad. Sci. USA 78, 2460–2464 (1981)] and the amount of BGH activity in the cellular extract was determined by immunoprecipitation.

The sequencing information for the bovine growth hormone gene produced is shown in Table 2.

EXAMPLE 2

Production of Interferon

1. Isolation of IFN mRNA 3.55 grams of Sendai virus induced lymphocytes were disrupted by means of a Dounce homogenizer into 40 ml of cold buffer (10° C.) consisting of 50 mM NaOAc, pH 5.2; 6 M guanidine HCl; and 0.1 M 2-mercaptoethanol. The resulting solution was sonicated at 60W pulsed power for 2×30 seconds and then layered onto 3 ml shelves of 5.8 M CsCl, pH 7.2, containing 0.1 M EDTA. The material was centrifuged at 15° C. in a Beckman Type 50 Ti rotor at 40,000 rpm overnight. The pellet was resuspended on ice for 20 minutes in 6.6 ml of the above cold buffer plus 20 mM EDTA, and then treated with 3.3 ml of ice-cold absolute ethanol. After 1 hour at −20° C., the precipitate was pelleted by a centrifugation at 8,000 rpm for 20 minutes at −10° C. The pellet was resuspended two times in 18 ml of the preceding buffer, treated with 9 ml of ice cold absolute ethanol, chilled one hour at −20° C. and the pellet collected as decribed previously. The final pellet was resuspended in 8 ml of 0.1 M EDTA with heating at 60° C., and then 0.1 volume of 2M NaOAC, pH 5.0, and 2 volumes of ice-cold absolute ethanol were added and the solution placed at −20° overnight. The RNA precipitate was collected by centrifugation at 8,000 rpm for 20 minutes at −10° C., and was dissolved in 5 ml water. The yield was 396 mg RNA. The RNA solution was diluted with 5 ml of 2× concentrated binding buffer (20 mM Tris-HCL, pH 7.5; 2 mM EDTA, pH 7.0; 0.4% SDS; and 0.24 M NaCl). The RNA was applied to a 1 ml oligo-dTcellulose column, the column was washed with 1× concentrated binding buffer and then the poly A-containing RNA (mRNA) was eluted by washing the column with binding buffer containing no NaCl. About 39 mg of poly A-containing RNA was obtained. A portion of the poly A-containing RNA was translated in vitro in a rabbit reticulocyte lysate system [Pelham, H.R.B. and Jackson, R.J., Eur. J. Biochem. 67, 247–256 (1976)] to confirm the isolation of mRNA coding for interferon.

2. Preparation of double-stranded copy DNA (cDNA)

About 2.5 μg of cDNA was synthesized from 25 μg of the lymphocyte poly A-containing RNA by incubation for one hour at 42° C. in 50 mM Tris-Hcl, pH 8.3; 100 mM KCl; 8 mM MgCl$_2$; 0.4 mM dithiothreitol; 1.2 mM each dATP, dGTP and dTTP; and 20 μg/ml oligo (—dT)$_{12-18}$, containing 100 units reverse transcriptase and 0.25 mM α-$^{32}$P-dCTP(1.8 Ci/mmole). After heating the reaction mixture at 100° C. for 3.5 minutes, quick chilling on ice for approximately 3 minutes and removing the precipitated protein by centrifugation, to the supernatant was added Hepes-NaOH, pH 6.9, to 100 mM; MgCl$_2$ to 5 mM; dithiothreitol to 0.5 mM; and deoxynucleoside triphosphates as above. Incubation of this mixture with 300 units of E. coli DNA polymerase I for 2.5 hours at 15° C. produced 1.8 μg of double-stranded cDNA. The DNA was phenol extracted, separated from unincorporated triphosphates by chromatography on Sephadex G-100 (13 ml column, 0.68 cm × 37 cm, eluted with 20 mM Tris-HCl, pH 7.5, 3.5 mM EDTA) and ethanol precipitated overnight at −20° C. by addition of 1/10 volume 2 M NaOAc, pH 5, and 2.5 volumes cold ethanol. The double-stranded cDNA was then treated with 8,000 units of S1 nuclease at 37° C. for one hour in buffer (0.3 M NaCl, 30 mM NaOAc, pH 4.6, 3 mM ZnSO$_4$). The reaction was terminated by addition of EDTA to 10 mM, and Tris-HCl, pH 8.3, to 200 mM, and the mixture applied to a Biogel A-150m column (0.7 cm × 35 cm) equilibrated and eluted with 10 mM Tris-HCl, pH 7.5, 250 mM NaCl and 1 mM EDTA. The peak fractions (0.5 ml each) of large molecular weight DNA were pooled and ethanol precipitated by addition of 1/10 volume 2 M NaOAC, pH 5, and 2.5 volumes cold absolute ethanol.

3. Addition of HindIII Linkers

The S1-treated double-stranded cDNA (0.21 μg) was incubated in buffer (60 mM Tris-HCl, pH 7.5; 8 mM MgCl; 5 mM dithiothreitol, 1 mM ATP and 1 mM of each deoxynucleoside triphosphate) with 9 units of E. coli DNA polymerase I at 10° C. for 10 minutes and then placed on ice. This blunt-ended double stranded cDNA was next incubated in 65 mM Tris-HCl, pH 7.5; MgCl$_2$; 5 mM dithiothreitol; 1 mM ATP, with 160 pmoles of $^{32}$P-labelled HindIII synthetic linker (100 × excess over cDNA ends) and 4 blunt-end units of T4 DNA ligase at 15° C. for 5 minutes, cooled on ice, heat treated to inactivate the ligase, treated with HindIII restriction endonuclease (New England Biolabs, 9 units) in 5.6 mM Tris-HCl, pH 7.5, 5.6 mM MgCl$_2$ at 37° C. for 4 hours 45 minutes and then phenol extracted. The reaction was fractionated on a Biogel A-150m column (0.7 cm × 31.5 cm). Fractions (0.5 ml each) containing high molecular weight DNA were pooled and ethanol precipitated.

This double stranded cDNA with HindIII cohesive termini was then ligated to f1 phage CGF4 double-stranded DNA which had been cut open with HindIII restriction endonuclease and treated with calf intestinal alkaline phosphatase by the method of H. Goodman and R. J. MacDonald [Goodman, H. M. and MacDonald, R. J., *Methods in Enzymol.* 68, 75–91 (1979)] to remove the terminal phosphates (Note: In order to produce phage CGF4, f1 phage R229 [Boeke, J. D., *Mol. Gen. Genet.* 181, 288–291 (1981)] was cut with EcoRI endonuclease, rendered blunt ended with T4 DNA polymerase and ligated with HindIII synthetic oligonucleotide linkers from Collaborative Research, Inc. of Lexington, Mass.) The ligation reaction contained 60 mM Tris-HCl, pH 7.5; 6 mM MgCl$_2$; 7 mM dithiothreitol; 0.12 μg double-stranded cDNA; 1.2 μg CGF4 DNA; 0.5 mM ATP and 450 cohesive end units of T4 DNA ligase. Ligation was for 19 hours at 15° C.

4. Transfection of E. coli DB4548 with recombinant CGF4 DNA

E. coli strain C GE6 (DB4548; hsdR$^-$, hsdM$^+$, sup E, sup F, B1$^-$, met$^-$) was grown in 150 ml tryptone broth at 37° C. with shaking and harvested at OD$_{700}$=0.5 by centrifugation at 7,000 rpm for 10 minutes at 4° C. The cells were resuspended in 70 ml ice cold 50 mM CaCl$_2$ and allowed to sit at 0° C. for 30 minutes. The suspension was then centrifuged at 7,000 rpm for 10 minutes at 4° C. and resuspended in 3 ml ice cold 50 mM CaCl$_2$. After standing at 0° C. for 2 hours the cells were used for transfection. Either 1 μl or 2 μl of 1:40 dilution of ligation reaction in 50 mM Tris-HCl, pH 7.5, was added to each of 12 tubes containing 50 μl sterile 50 mM Tris-HCl, pH 7.5. One-tenth milliliter of the CaCl$_2$-treated cells was added to each tube and the mixtures set on ice for 30 minutes. After warming to 37° C. for 2 minutes, 0.2 ml of CGE5 (JM1: J. Messing (1979), F'traD36 proAB lacIZ $\nabla$M15 in a Δlac pro) SupE thi$^-$ background) overnight culture and 3 ml of 0.7% soft agar were added, and the mixture poured into tryptone agar plates. Incubation at 37° C. overnight produced over 1280 plaques.

5. Identification of a recombinant-CGF4 carrying the leukocyte interferon sequence The plaques were transferred to nitrocelluloses and probed as described by Benton and Davis [Benton, W. D. and Davis, R. W., *Science* 196, 180–182 (1977)] using a $^{32}$P-labelled synthetic oligonucleotide (with the sequence, CATGATTTCTGCTCTGAC, Collaborative Research, Inc.) which corresponds to a known segment of LeIFN. The oligonucleotide (1 μg) was kinased with 0.5 mC. γ-$^{32}$-P-ATP using 6 units of T4 polynucleotide kinase (P-L Biochemicals) in a 20 μl reaction containing 66 mM Tris-HCl, pH 7.5, and 10 mM MgCl$_2$. The phage which hybridized intensely to the synthetic oligonucleotide probe were picked from the plates and stored in TY medium at 4° C. Samples of the intact phage were amplified by growth overnight on CGE5 cells, harvested by centrifugation, and subjected to electrophoresis in a 0.6% agarose gel containing 0.37 M Tris-glycine, pH 9.5, and stained with ethidium bromide after treatment in 0.2 N NaOH for one hour and neutralization in 0.5 M Tris-HCl, pH 7.4. The migration is inversely proportional to the log of the size of the phage DNA and allowed selection of phage carrying inserted IFN DNA of size of 1000 to 1200 base pairs. Double-stranded RF1 DNA was prepared from the phage by the method of Moses et al. [Moses, P. B., Boeke, J. D., Horuchi, K. and Zinder, N. D., *Virology* 104, 267–273 (1980)]. This DNA was cut with HindIII restriction endonuclease and the resulting fragments analyzed on an agarose gel to confirm that the insert was in the HindIII site and of the anticipated size. One of the phage DNA's which has an insert of about 1200 base pairs (bp) was chosen for further study. The DNA insert was sequenced by the method of Maxam and Gilbert [Maxam, A. M. and Gilbert, W., *Methods in Enzymol* 68, 499–560 (1980)].

6. Expression of LeIFN in *Saccharomyces cerevisiae*

Figure 5:
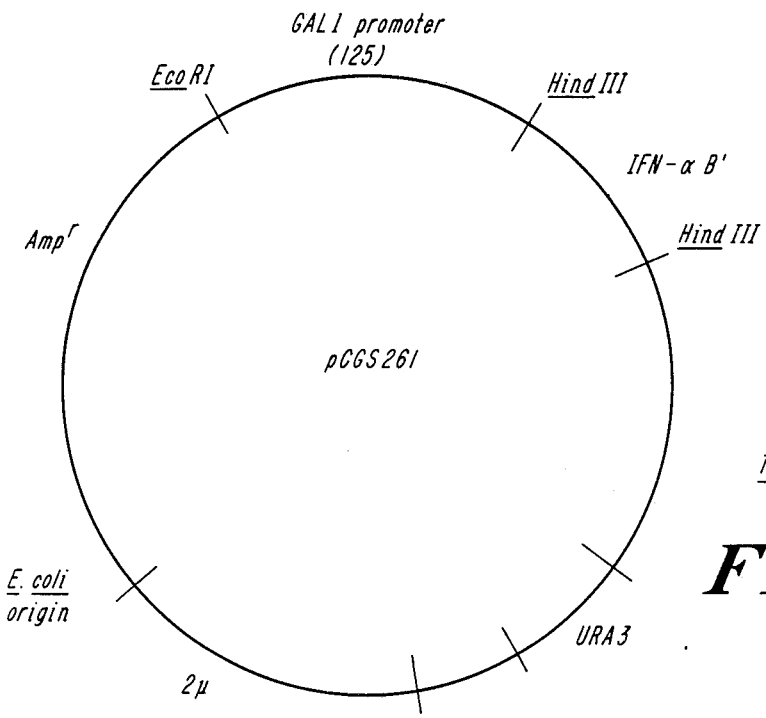

A plasmid, pCGS261, as seen in FIG. 5, designed to facilitate obtaining expression of LeIFN in yeast was constructed. In order to produce the LeIFN in yeast, an ATG initiation codon was incorporated at the 5'-side of the first codon (TCT for cysteine) of mature, processed IFN. Based on the fact that Sau3AI cuts at the 3'-side of the first codon, an oligonucleotide (ACACATC-GATGTGT) which is recognized by ClaI and also contains the ATG-TGT sequence was synthesized by Collaborative Research, Inc. A Sau3AI fragment which codes the amino acid residues 2 to 61 was purified by digesting 30 μg of the HindIII 1.2 kilobase fragment with 10 units Sau3AI restriction endonuclease in a 50 μl reaction volume containing 10 mM Tris-HCl, pH 7.5; 10 mM MgCl$_2$; and 60 mM NaCl for 4 hours at 37° C. The DNA fragment was purified by polyacrylamide gel electrophoresis. The DNA was phenol extracted and preciPitated with ice-cold absolute ethanol. The cohesive ends were filled in by treating the DNA with 4 units E. coli DNA Polymerase I Klenow fragment and 0.1 mM each nucleoside triphosphate in 66 mM Tris-HCl, pH 7.5; 66 mM NaCl; 66 mM MgCl$_2$ and 66 mM dithiothreitol, for 30 minutes at room temperature.

The above synthetic oligonucleotide was ligated onto the Sau3AI fragment in 66 mM Tris-HCl, pH 7.5; 10 mM MgCl$_2$; 10 mM 2-mercaptoethanol; 1 mM ATP with 500 pmole 32P-oligonucleotide (5 μg); 4 pmoles DNA (20 μg) and 4 blunt-end units of T4 DNA ligase at 17° C. overnight. This ligation created an ATG initiation codon and restored the first codon TGT. ClaI polylinker was removed by treating the fragment with 20 units restriction endonuclease ClaI for 3 hours at 37° C. in a 20 μl reaction containing 10 mM Tris-HCl, pH 7.5; 10 mM MgCl$_2$; and 1 mg/ml bovine serum albumin. The resulting fragment was cloned into the ClaI site of plasmid pBR322. The plasmid (10 μg) was cut with the restriction endonuclease ClaI (New England Biolabs, 20 units) for 2 hours at 37° C. in a 20 μl reaction containing 10 mM Tris-HCl, pH 7.5; 10 mM MgCl$_2$ and 1 mg/ml bovine serum albumin. The preparation of restriction cut plasmid was phenol extracted, ethanol precipitated and treated with calf intestinal phosphatase by the method of H. Goodman and R. J. MacDonald [Goodman, H. M. and MacDonald, R. J., *Methods in Enzymology* 68, 75–91 (1979)] to remove the terminal phosphates. Approximately 0.5 pmole of the ClaI fragment and 0.3 pmole of the ClaI cut plasmid were ligated together at 15° C. for 3 hours in a 20 μl reaction containing 66 mM Tris-HCl, pH 7.5; 6 mM MgCl$_2$; 10 mM dithiothreitol; 1mM ATP; and T4 DNA ligase (New England Biolabs, 300 units) creating plasmid pCGE32. Transformation-competent E. coli strain CGE43 (LG90; F$^-$Δ(lac-pro)xlll) was prepared as described previously for CGE6, and 5 μl of the ligated DNA was mixed with 200 μl of the cells for 30 minutes at 0° C., heat treated at 37° C. for 2 minutes, incubated at 18° C. for 10 minutes, and diluted five-fold with fresh tryptone broth. After incubation for 30 minutes at 37° C. with shaking, cells were plated on tryptone plates containing ampicillin (20 μg/ml). Ampicillin-resistant colonies were picked, and the plasmid DNA was prepared and analyzed by restriction enzyme digestion. By these criteria several cells carried the desired plasmid, pCGE32.

The rest of the IFN gene was put back together by using the EcoRI site located in the region coding for amino acid residue 37. Plasmid pCGE32 DNA (10 μg) was cut with the restriction endonuclease HindIII (Collaborative Research, Inc., 12 units) for 2 hours at 37° C. in a 20 μl reaction containing 10 mM Tris-HCl, pH 7.5; 10 mM MgCl$_2$; 60 mM NaCl; and 1 mg/ml bovine serum albumin). This DNA was next digested with the endonuclease EcoRI (Collaborative Research, Inc., 15 units) for 3 hours at 37° C. in a 20 μl reaction containing 100 mM Tris-HCl, pH 7.6; 10 mM MgCl$_2$; 30 mM NaCl; and 1 mg/ml bovine serum albumin. The restriction cut DNA was phenol extracted, ethanol precipitated, redissolved in water and applied to a preparative horizontal 1.5% agarose gel. After electrophoresis for 2 to 3 hours in 40 mM Tris-acetate, pH 7.2, the gel was stained with ethidium bromide and examined under long wavelength ultraviolet light. The digested HindIII to EcoRI band which codes the ATG-TGT to amino acid residue 37 was excised and the DNA extracted by freezing and thawing the gel pieces [Thuring, et al., *Anal. Biochem* 66, 213 (1975)]. The DNA fragment was ethanol-precipitated and redissolved in water. The plasmid (20 μg) containing the IFN clone was cut with the restriction endonuclease HindIII (New England Biolabs, 180 units) for 2 hours at 37° C. as above and then the DNA (12 μg) was cut with the restriction endonuclease EcoRI (New England Biolabs, 24 units) for 6 minutes at 37° C. The restriction cut DNA was phenol extracted, ethanol precipitated, and redissolved in water. This EcoRI to HindIII fragment coding for amino acid residue 37 to the 3'-nontranslating region of IFN was analyzed by gel electrophoresis and excised from the gel (see above). Approximately 0.25 pmole of each fragment were ligated together into plasmid pBR322 opened at its HindIII site (see above) for 4 hours at 14° C. in a 20 μl reaction containing 66 mM Tris-HCl, pH 7.6; 6.6 mM MgCl$_2$; 10 mM dithiothreitol; 1 mM ATP and T4 DNA ligase (New England Biolabs, 300 units). Transformation-competent E. coli strain CGE43 cells were prepared exactly as described above, and 5 μl of the ligated DNA was mixed with 100 μl of the cells for 30 minutes at 0° C., heat treated at 37° C. for 2.5 minutes, and diluted ten-fold with fresh tryptone broth. After incubation for 30 minutes at 37° C. with shaking, cells were plated on tryptone plates containing ampicillin (20 μg/ml). Ampicillin-resistant colonies were picked, and the plasmid DNA was prepared and analyzed by restriction enzyme digestion. By these criteria several strains carried the desired plasmid, pCGE38.

A HindIII site was constructed in pCGS109 which is a standard shuttle vector (pC GS42) with P$_{GAL1}$ inserted between the EcoRI and BamHI sites. The vector, pCGS109, was cut with BamHI restriction enzyme, digested with S1 nuclease to remove cohesive ends making it blunt-ended and then ligating on HindIII linker. The vector was treated with HindIII restriction enzyme and then the cohesive ends were ligated together to produce the vector pCGS135. The 1.1 kilobase HindIII fragment containing the gene for LeIFN was isolated from plasmid pCGE38 (30 μg) by cutting the plasmid with restricton endonuclease HindIII for 1.5 hours at 37° C. as above. The restriction cut DNA was phenol extracted, ethanol precipitated, redissolved in water and applied to a preparative 1% agarose gel. After electrophoresis in 40 mM Tris-acetate, pH 7.2, the gel was stained with ethidium bromide and examined under long wavelength ultraviolet light. The 1.1 kilobase band was excised and the DNA extraced by freezing and thawing the gel pieces [Thuring, et al., *Anal. Biochem.* 66, 213 (1975)]. The DNA fragment was ethanol precipitated and redissolved in water. Approximately 0.2 μg of the HindIII fragment was ligated into plasmid pCGS135 (1 μg) opened at its HindIII site adjacent to the P$_{GAL1}$ region. Ligation of the vector and IFN fragment was carried out at 14° C. in a 20 μl reaction containing 66 mM Tris-HCl, pH 7.6; 6.6 mM MgCl$_2$; 10 mM dithiothreitol; 1 mM ATP and T4 DNA ligase (Collaborative Research, Inc., 10 units).

The yeast strain CGY528 (αura 3-52, his 4-29, pep 4-3, GAL+) was transformed with the plasmid DNA by the method of A. Hinnen, J. B. Hicks, and G. Fink [Hinnen, A., Hicks, J. B. and Fink, G. F., *Proc. Nat. Acad. Sci. USA* 75, 1929–1933 (1978)]. Yeast transformant CGY528, capable of growth without added uracil due to the presence of URA3 gene on the plasmid was picked. (Strain CGY528 bearing plasmid pCGS261 is on deposit with the American Type Culture Collection (ATCC), Accession Number 20663, deposited February 1983.) The yeast cells were grown at 30° C. with agitation in a medium containing 6.7 g/l yeast nitrogen base, 20 μg/l histidine and 2% galactose. The synthesis of interferon was verified by collecting cells grown to Klett=50 (10$^7$ cells/ml) by centrifugation, resuspended in 0.25 ml 0.05 M Tris-HCl, pH 7.6, 20% glycerol and 1 mM PMSF, and frozen at −20° C. The cells were disrupted by glass beads by the method of M. Rose, et al. [Rose, M., Casadaban, M. J. and Botstein, D., *Proc. Nat. Acad. Sci. USA* 78, 2460–2464 (1981)] and the amount of interferon activity in the cellular extract was determined by conventional methods to be 10$^5$ units/mg of soluble protein.

The sequencing information for the human leukocyte interferon gene produced is shown in Table 3.

TABLE 3

```
      -40              -30              -20              -10               1
CAAGCTTG GTC ATC CAT CTG A ACC AGC TCA G CAG CAT CCA C AAC ATC TAC A ATG GCG TTG ACT TTT TAT TTA CTG GCC CTA GTG GTG GTG
                                                             MET ALA LEU THR PHE TYR LEU LEU ALA LEU VAL VAL VAL
                                                               1                              10                       
 40              50              60              70              80              90             100             110             120
CTC AGC TAC AAG TCA TTC AGC TCT CTG GGC TGT GAT CTG CCT CAG ACT CAC AGC CTG GGT AAC AGG AGG GCC TTG ATA CTC
LEU SER TYR LYS SER PHE SER SER LEU GLY CYS ASP LEU PRO GLN THR HIS SER LEU GLY ASN ARG ARG ALA LEU ILE LEU
              20                          30                           40

130             140             150             160             170             180             190             200
CTG GCA CAA ATG CGA AGA ATC TCT CCT TTC TCC TGC CTG AAG GAC AGA CAT GAC TTT GAA TTC CCC CAG GAG GAG TTT GAT
LEU ALA GLN MET ARG ARG ILE SER PRO PHE SER CYS LEU LYS ASP ARG HIS ASP PHE GLU PHE PRO GLN GLU GLU PHE ASP
              50                           60

210             220             230             240             250             260             270             280
GAT AAA CAG TTC CAG AAG GCT CAA GCC ATC TCT GTC CTC CAT GAG ATG ATC CAG CAG ACC TTC AAC CTC TTC AGC ACA AAG
ASP LYS GLN PHE GLN LYS ALA GLN ALA ILE SER VAL LEU HIS GLU MET ILE GLN GLN THR PHE ASN LEU PHE SER THR LYS
              70                           80                           90

290             300             310             320             330             340             350             360
GAC TCA TCT GCT GCT TGG GAT GAG ACC CTT CTA GAT AAA TTC TAC ATC GAA CTT CTA CAA CAG CTG AAT GAC CTG GAG TCC
ASP SER SER ALA ALA TRP ASP GLU THR LEU LEU ASP LYS PHE TYR ILE GLU LEU LEU GLN GLN LEU ASN ASP LEU GLU SER
             100                          110                          120

370             380             390             400             410             420             430             440
TGT GTG ATG CAG GAA GTG GGG GTG ATA GAG TCT CCC CTG ATG AAC GAG GAC TCC ATC CTG GCT GTG AGG AAA TAC TTC CAA
CYS VAL MET GLN GLU VAL GLY VAL ILE GLU SER PRO LEU MET ASN GLU ASP SER ILE LEU ALA VAL ARG LYS TYR PHE GLN
             130                          140

450             460             470             480             490             500             510             520
AGA ATC ACT CTA TAT CTG ACA GAG AAG AAA TAC AGC AGC TGT GCC TGG GAG GTT GTC AGA GCA GAA ATC ATG AGA TCC TTC
ARG ILE THR LEU TYR LEU THR GLU LYS LYS TYR SER SER CYS ALA TRP GLU VAL VAL ARG ALA GLU ILE MET ARG SER PHE
             150                          160                          170

530             540             550             560             570             580             590             600
TCT TTA TCA ATC AAC TTG CAA AAA AGA TTG AAG AGT AAG GAA TGA GACCTGGTAC AACACGGAAA TGATTCTTAT AGACTAATAC
SER LEU SER ILE ASN LEU GLN LYS ARG LEU LYS SER LYS GLU
             180

610             620                630              640              650              660             670              680              690              700              710
AGCAGCTCAC ACTTCGACAA GTTGTGCTCT TTCAAAGACC CTTGTGTTCT GCCAAAAACCAT GCTATGAATT GAATCAAATG TGTCAAGTGT TTTCAGGAGT 720              730              740              750              760              770              780              790              800              810
GTTAAGCAAC ATCCTGTTCA GCTGTATGGG CACTAGTCCC TTACAGATGA CCATGCTGAT GGATCTATTC ATCTATTTAT TTAAATCTTT ATTTAGTTAA 820              830              840              850              860              870              880              890              900              910
CTATCTAGAG GGCTTAAATT AGTTTTGGTTC ATATTATATT ATGTGAACTT TTATATTGTG CAAAAACATG TTCZZZATAT TTATTATTTT 920              930              940              950              960              970              980              990             1000             1010
GCCTTGTTTA TTAAATTTTT ACTATAGAAA AATTCTTTAT TTATTCTTTA AAATTGAACT CCAACCCTGA TTGTGCAAAC TGATTAAAGG AAGTGGTGCA
```

TABLE 3-continued

```
        1020       1030       1040       1050       1060       1070       1080       1090       1100       1110
CTTGCAAACA AGCTCTACTA TCCCTGAGGA AATACCAGAG ACTCTGAAG GTGATATTCA AAAAGCAAAA AGCAAAATTC TAACACTAAT TGAACCTGAC
        1120       1130       1140       1150       1160       1170       1180       1190
ATTAAAACAG CACAGATGAC TGCTACCATA GATTCCTGCC TTTCAAACGC AGGGCAAGAC ATTCATTGGT CATACGTAGA AGGC CAAGCTG
```

EXAMPLE 3

Production of Prorennin

1. Isolation of the RNA

Stomach tissue from milk-fed calves was obtained fresh from a local slaughterhouse; the mucosa of the fourth stomach was dissected away from the stomach wall and frozen in dry ice. Twenty-one grams of the mucosal tissue was disrupted by means of a blender into 200 ml of cold buffer (10 degrees C.) consisting of 50 mM Tris.HCl, pH 7.5, 8M guanidine HCl, and 1 mM dithiothreitol. Insoluble material was removed by centrifugation in a Sorvall SA-600 rotor at 10,000 rpm for 12 minutes. To the 200 ml of supernatant from the spin was added 100 ml of ice cold absolute ethanol. After 1.5 hours at −20 degrees C., the precipitate was pelleted by a centrifugation at 3000 rpm for 30 minutes at −10 degrees C. The pellet was dissolved in 40 ml of ice cold buffer (EGAD) consisting of 20 mM EDTA, pH 7, 20 mM NaOAc, pH 7, 8M guanidine.HCl, and 1 mM dithiothreitol. Twenty milliliters of cold absolute ethanol was added and the solution placed at −20 degrees C. for 45 minutes. The precipitate was pelleted by centrifugation at 3000 rpm for 20 minutes at −10 degrees C. The pellet was redissolved in 40 ml cold EGAD buffer and the precipitation with 20 ml cold ethanol, centrifugation and redissolving the pellet in EGAD buffer was repeated two additional times. Finally, the pellet was dissolved in 16 ml of 20 mM EDTA, pH 7 and extracted three times with chloroform:isobutanol (4:1). Next, two volumes of 4.5M NaOAc PH 5.2 was added to the aqueous layer and the solution was placed at −20 degrees C. overnight. The RNA precipitate was collected by centrifugation at 10,000 rpm for 25 minutes at −10 degrees C., and was dissolved in 30 ml water. The yield was 45 mg RNA. The RNA was precipitated by addition of 1 ml of 2M NaOAc pH 5 and 75 ml absolute ethanol, followed by incubation at −20 degrees C. overnight. The RNA was pelleted by centrifugation (10,000 rpm, 10 minutes −10 degrees C.) and redissolved in 20 ml water, heated to 60 degrees C. for 10 minutes, chilled rapidly on ice and diluted with 21 ml of 2× concentrated binding buffer (20 mM Tris.HCl pH 7.5, 2 mM EDTA pH 7, 0.4% SDS and 0.24M NaCl). The RNA was applied to a 4 ml oligo-dT-cellulose column, the column was washed with 45 ml of 1× concentrated binding buffer, and then the poly A-containing RNA was eluted by washing the column with binding buffer containing no NaCl. About 1 mg of poly A-containing RNA was obtained. A portion of the poly A-containing RNA was translated in vitro in a rabbit reticulocyte lysate system (H. R. B. Pelham and R. J. Jackson [1976] *Eur J. Biochem.* 67 247–256). The protein products were analyzed on a 10% polyacrylamide gel. A single major protein band was observed which was precipitated with rennin antiserum showing that rennin mRNA is present in the poly A-containing RNA.

2. Preparation of double-stranded copy DNA (cDNA)

About 8.7 μg of cDNA was synthesized from 20 μg of the calf stomach poly A-containing RNA by incubation for one hour at 42 degrees C. in 50 mM Tris.HCl pH 8.3, 100 mM KCl, 8 mM $MgCl_2$, 0.4 mM dithiothreitol, 1 mM each deoxynucleoside triphosphate, 20 μg/ml oligo(-dT)$_{12-18}$ containing 100 units reverse transcriptase and 1 Ci/mmole $\alpha^{32}$P-dCTP. After heating the reaction mixture at 100 degrees C. for 3 minutes, chilling on ice for 3 minutes and removing the precipitated protein by centrifugation, to half the supernatant material was added Hepes.KOH pH 6.9 to 100 mM, $MgCl_2$ to 5 mM, dithiothreitol to 0.5 mM, deoxynucleoside triphosphates to 0.125 mM. Incubation of this mixture with 300 units of *E. coli* DNA polymerase I for 2 hours at 16° C. produced 8.6 μg of double-stranded cDNA. The DNA was phenol extracted and separated from unincorporated triphosphates by chromatography on Sephadex G-100 (12 ml column, 0.7 cm×30 cm, eluted with 20 mM Tris.HCl pH 7.5, 0.5 mM EDTA) and was ethanol precipitated overnight at −20 degrees C. by addition of 1/10 volume 2M NaOAc pH 5, and 2.5 volumes cold ethanol. The double-stranded cDNA (4.6 μg) was then treated with 1000 units of S1 nuclease at 37 degrees C. for 1 hour in Buffer S (0.3M NaCl, 30 mM NaOAc, pH 4.6, 3 mM $ZnSO_4$). The reaction was terminated by addition of EDTA to 10 mM, and Tris.HCl pH 8.3 to 200 mM, and the mixture applied to a Biogel A-150m column (0.7 cm×33 cm) equilibrated and eluted with 10 mM Tris.HCl pH 7.5, 1 mM EDTA and 250 mM NaCl. The peak fractions (0.5 ml each) of large molecular weight DNA were pooled and ethanol precipitated by addition of 1/10 volume 2M NaOAC pH 5 and 2.5 volumes cold absolute ethanol.

3. Addition of HindIII Linkers

The S1-treated double-stranded cDNA (1.7 μg) was incubated in Buffer T (25 mM Tris.HCl pH 8, 6.6 mM $MgCl_2$, 0.5 mM EDTA, 5 mM 2-mercaptoethanol and 0.5 mM of each deoxynucleoside triphosphate) with 2 units of $T_4$ DNA polymerase at room temperature for 30 minutes. The material was phenol extracted and ether extracted and ethanol precipitated by addition of 1/10 volume 2M NaOAc pH 5 and 2.5 volumes ethanol. This blunt-ended double-stranded cDNA was next incubated in 66 mM Tris.HCl pH 7.6, 6.6 mM $MgCl_2$, 5 mM 2-mercaptoethanol, 0.5 mM ATp, with 300 pmoles of $^{32}$P-labelled HindIII synthetic linker (100× excess over cDNA ends) and 9 blunt-end units of $T_4$ DNA ligase at 12 degrees overnight.

The reaction was adjusted to 10 mM EDTA pH 8 and fractionated on a Biogel A-150 m column (0.7 cm×20 cm. . Fractions (0.25 ml each) containing high molecular weight DNA were pooled and ethanol precipitated. This material was treated with HdIII restriction endonuclease (9 units) in 5.6 mM Tris.HCl pH 7.6, 5.6 mM $MgCl_2$ at 37 degrees C. for 45 minutes, then phenol extracted, ether extracted and ethanol precipitated by the addition of 1/10 volume 1M NaOc pH 5 and 2.5 volume, absolute ethanol. This double-stranded cDNA with Hind III cohesive termini was then ligated to f1 phage CGF4 double-stranded DNA which had been cut open with Hind III restriction endonuclease and treated twice with calf intestinal phosphatase by the method of H. Goodman and R. J. MacDonald (H. M. Goodman and R. J. MacDonald [1979] *Methods in Enzymology* 68, 74–91) to remove the terminal phosphates (Note: In order to produce phage CGF4, f1 phage R229 (J. D. Boecke [1981 ] *Mol. Gen. Genet.* 181, 288–291) was cut with EcoRI endonuclease, rendered blunt-ended with T4 DNA polymerase and ligated with Hind III synthetic oligonucleotide linkers from Collaborative Research, Inc. of Waltham, Mass.). The ligation reaction contained 66 mM Tris.HCl pH 7.6, 6.6 mM $MgCl_2$, 5 mM 2-mercapto-ethanol, 0.3 μg double-stranded cDNA, 0.2 μg CGF4 DNA, 0.5 mM ATP and 300 cohesive-end units of $T_4$ DNA ligase. Ligation was for 29 hours at 16 degrees C.

4. Transfection of *E. coli* BNN45 with recombinant-CGF4 DNA

*E. coli* strain CGE6 (BNN45; hsdR$^-$, hsdM$^+$, sup E, sup F, B1$^-$, met$^-$) was grown in tryptone broth at 37 degrees C. with shaking and harvested at OD$_{700}$=0.5 by centrifugation at 7000 rpm for 10 minutes at 4 degrees C. The cells were resuspended in ice cold 50 mM CaCl$_2$ (one-half the original culture volume) and allowed to sit at 0 degrees C. for 30 minutes. The suspension was then centrifuged at 7000 rpm for 10 minutes at 4 degrees C. and resuspended in 1/20 the original culture volume ice cold 50 mM CaCl$_2$. After standing at 0 degrees C. for 60 minutes the cells were used for transfection. One-half microliter of the 20 μl ligation reaction was added to each of 8 tubes containing 50 μl sterile 50 mM Tris.HCl pH 7.6. One-tenth milliliter of the CaCl$_2$-treated cells was added to each tube and the mixtures sat on ice for 30 minutes. After warming to 37° C. for two minutes, 0.2 ml of a CGE5(JM101:J. Messing [1979], F'tra D36 pro AB lac IZ M15 in a (lac pro) SupEthi$^-$ background) overnight culture and 3 ml of 0.7% soft agar were added, and the mixture poured onto eight tryptone agar plates. Incubation at 37 degrees C. overnight produced about 250 plaques per plate.

5. Identification of a Recombinant CGF4 carrying the rennin coding sequence

The plaques were transferred to to nitrocellulose and probed as described by Benton & Davis (W. D. Benton and R. W. Davis [1977] *Science* 196, 180–182) using $^{32}$P-labelled cDNA made from the calf-stomach poly A-containing RNA using α$^{32}$P-dCTP and reverse transcriptase (T. P. St. John and R. W. Davis [1979] *Cell* 16 443–452). About 80 recombinant phage which hybridize intensely to the labelled cDNA were picked from the plates and stored in TY medium at 4 degrees C. Samples of the intact phage were amplified by growth overnight on CGE5 cells, harvested by centrifugation, and subjected to electrophoresis in a 2% agarose gel containing 0.37M Tris.glycine pH 9.5 and stained with ethidium bromide after treatment in 0.2N NaOH for one hour and neutralization in 0.5M Tris.HCl pH 7.4. The migration is inversely proportional to the log of the size of the phage DNA and allowed selection of eight phage carrying inserted DNA of size 1000 to 2000 base pairs.

Double-stranded RFI DNA was prepared from these eight p'ages by the method of Moses et al (P. B. Moses, J. D. Boeke, K. Horiuchi & N. D. Zinder [1980] *Virology* 104, 267). This DNA was cut with Hind III and the resulting fragments analyzed on an agarose gel to confirm that the insert was in the Hind III site and of the anticipated size. Finally, the DNA from four of the recombinant phages (approximately 5–10 μg from each) and DNA from the vector CGF4 was cut with Hind III and the fragments, after denaturation by boiling for 45 seconds and freezing in dry ice/ethanol, were bound to nitrocellulose by spotting the DNA in water onto small pieces of nitrocellulose pretreated with 20× SSC and dried. After baking in vacuo at 75 degrees C. for 1.5 hours, the DNA bound to nitrocellulose was carried through the hybrid selection procedure as described by Miller et al (J. S. Miller, R. P. Ricciardi, B. E. Roberts, B. M. Paterson & M. B. Mathews [1980] *J. Mol. Biol.* 142, 455–488) using 2 μg poly A-enriched calf stomach RNA for each hybridization. The eluted RNA was then translated in a reticulocyte lysate system labelling with $^{35}$S-methionine by the method of pelham and Jackson (H. R. B. Pelham & R. J. Jackson [1976] *Eur. J. Biochem.* 67, 247–256) and the resulting protein products analyzed on a 10% polycrylamide gel containing 0.1% SDS according to Laemmli (U. Laemmli [1970] *Nature* 227, 680–685). The results of the gel analysis indicated that all four of the phage DNAs tested did hybridize to the rennin mRNA since all four selected an RNA species which, upon translation in a rabbit reticulocyte lysate, yields a protein product identical to pre-prorennin in size and immunological criteria. Two of the four, 293-207 which has an insert of about 1400 base pairs (bp) and 293-118/37 which has an insert of about 1250 bp, were chosen for further study. The DNA inserts were sequenced by the method of Maxam and Gilbert (A. M. Maxam and W. Gilbert [1980] *Methods in Enzymology* 68, 499–560). From nucleotide 205 to 1350 is the DNA sequence for the pre-prorennin A gene (see Table 9). The nucleotide sequences 1–204 and 1351 to 1460 are attached to the pre-prorennin but can be removed if desired and are not Ⓡssential to use of the gene in expression. Useful portions of the DNA material of Table 3 can be separated and used by known techniques.

TABLE 4

```
                                30                            60                              90
AAG CTT GGG CGA GCG AGG GGT AGG CCA GGA TCC CGT CGA ATT CGG CAT AGG CCC CGG GCT CCT GGG TGC TCA GGC 120                           150                             180
CTA CTG TCT GCT GGA TGT CCA CAA TGT TGG AGA CAG TGA CAG CGG TGT CAT AGC CCA GGA TGC CCT GCA TGC CTG TCC CGT AGT GGA TAG 210                           240                             270
ACA GCG GCT GGA CCC AGA TCC AAG ATG AGG TGT CTC GTG GTG CTA CTT GCT GTC GTC TCC CAG GGC GCT CTC TCC GAG ATC ACC AGG ATC
                              MET ARG CYS LEU VAL VAL LEU LEU ALA VAL VAL SER GLN GLY ALA LEU SER GLU ILE THR ARG ILE 300                           330                             360
GCT CTG TAC AAA GGC AAG TCT CTG AGG AAG GAG CAT GGG CTT AAG GAC TTC CTG GAG GAC TTC CTG CAG AAA CAG TAT GGC ATC AGC
PRO LEU TYR LYS GLY LYS SER LEU ARG LYS GLU HIS GLY LEU LYS LEU ASP PHE LEU GLU ASP PHE LEU GLN LYS GLN TYR GLY ILE SER 390                           420                             450
AGC AAG TAC TCC GGC TTC GGG GAG GTG CCC AGC GTG GCC AGC GTG CCC CTG ACC AAC TAC CTG GAT AGT CAG TAC TTT GGG AAG ATC TAC CTC GGG ACC
SER LYS TYR SER GLY PHE GLY GLU VAL PRO SER VAL ALA SER VAL PRO LEU THR ASN TYR LEU ASP SER GLN TYR PHE GLY LYS ILE TYR LEU GLY THR 480                           510                             540
CCG CCC CAG GAG CGC TTC ACC GTG CTG TTT GAC ACT GGC TCC TCT GAC TTC TGG GTA CCC TCT ATC TAC TGC AAG AGC AAT GCC TGC AAA AAC
PRO PRO GLN GLU ARG PHE THR VAL LEU PHE ASP THR GLY SER SER ASP PHE TRP VAL PRO SER ILE TYR CYS LYS SER ASN ALA CYS LYS ASN 570                           600                             630
CAC CAG CGC TTC GAC CCG CAA GAC CTG GTG TCC TTC CAG AAC TAC ACC TCT ATC CAC TAC GGC AAG CCC CTG GGC ACA GGC AGC ATG CAG GGC
HIS GLN ARG PHE ASP PRO ARG LYS SER SER THR PHE GLN ASN TYR THR SER ILE HIS TYR GLY LYS PRO LEU GLY THR GLY SER MET GLN GLY 660                           690                             720
ATC CTG GGC TAT GAC ACC GTC ACT GTC TCC AAC ATT GTG GAC ATC CAG CAG ACA GTA GGC CTG AGC ACC CAG GAG CCC GGG GAC GTC TTC
ILE LEU GLY TYR ASP THR VAL THR VAL SER ASN ILE VAL ASP ILE GLN GLN THR VAL GLY LEU SER THR GLN GLU PRO GLY ASP VAL PHE 750                           780                             810
ACC TAT GCC GAA TTC GAC GGG ATC CTG GGG ATG GCC TAC CCC TCG CTG GCC TCA GAG TAC TCG ATA CCC GTG TTT GAC AAC ATG ATG AAC
THR TYR ALA GLU PHE ASP GLY ILE LEU GLY MET ALA TYR PRO SER LEU ALA SER GLU TYR SER ILE PRO VAL PHE ASP ASN MET MET ASN 840                           870                             900
AGG CAC CTG GTG GCC CAA GAC CTG TTC TCG GTT TAC ATG GAC AGG AAT GGC CAG GAG CAG ATG CTC ACG CTG GGG GCC ATC GAC CCG TCC
ARG HIS LEU VAL ALA GLN ASP LEU PHE SER VAL TYR MET ASP ARG ASN GLY GLN GLU GLN MET LEU THR LEU GLY ALA ILE ASP PRO SER 930                           960                             990
TAC TAC ACA GGG TCC CTG CAC TGG GTG CCC GTG ACA GTG CAG CAG TAC TGG CAG TTC ACT GTG GAC AGT GTC ACC ATC AGC GGT GTG GTT
TYR TYR THR GLY SER LEU HIS TRP VAL PRO VAL THR VAL GLN GLN TYR TRP GLN PHE THR VAL ASP SER VAL THR ILE SER GLY VAL VAL 1020                          1050                            1080
GTG GCC TGT GAG GGT GGC TGT CAG GCC ATC CTG GAC ACG GGC ACC TCC AAG CTG GTC GGG CCC AGC AGC GAC ATC CTC AAC ATC CAG CAG
VAL ALA CYS GLU GLY GLY CYS GLN ALA ILE LEU ASP THR GLY THR SER LYS LEU VAL GLY PRO SER SER ASP ILE LEU ASN ILE GLN GLN 1110                          1140                            1170
GCC ATT GGA GCC ACA CAG AAC CAG TAC GGT GAG TTT GAC ATC GAT TGC GAC AAC CTG AGC TAC ATG CCC ACT GTG GTC TTT GAG AAT CAT CCC AAT
ALA ILE GLY ALA THR GLN ASN GLN TYR GLY GLU PHE ASP ILE ASP CYS ASP ASN LEU SER TYR MET PRO THR VAL VAL PHE GLU ASN HIS GLN 1200                          1230                            1260
GGC AAA ATG TAC CCA CTG ACC CCA TCA CAG TAC ACC AGC CAG GAC CAG GGC TTC TGT ACC AGT GGC TTC CAG AGT GAA AAT CAT TCC CAG
GLY LYS MET TYR PRO LEU THR PRO SER GLN TYR THR SER GLN ASP GLN GLY PHE CYS THR SER GLY PHE GLN SER GLU ASN HIS SER GLN
```

TABLE 4-continued

```
                                     1290                                            1320                                            1350
AAA TGG ATC CTG GGG GAT GTT TTC ATC CGA GAG TAT TAC AGC GTC TTT GAC AGG GCC AAC AGG GCC AAC CTC GTG GCC AAA GCC ATC TGA
LYS TRP ILE LEU GLY ASP VAL PHE ILE ARG GLU TYR TYR SER VAL PHE ASP ARG ALA ASN ARG ALA ASN LEU VAL GLY LEU ALA LYS ALA ILE
                                     1380                                            1410                                            1440
TCA CAT CGC TGA CCA AGA ACC TCA TGC TGC OCA CAC ACC TGC ACA CAC ACA TGC ACA CAC ACA CAT GTA CAT GGC ACA TGT GCA CAC ACA CAG ATG
AGG TTT CCA GAC CCA AGC TT
```

This Table combines information from both 293-207 and 293-118/37: recombinant phage 293-207 carries an insert bearing the sequence shown in Table 9 from nucleotide #1 to at least nucleotide #1360 except for nucleotides 848-961 which are deleted, while phage 293-118/37 carries an insert bearing the sequence from nucleotide #229 to nucleotide #1460. As revealed by the sequencing results, initiation of rennin synthesis occurs at a methionine codon (nucleotides 205-207) and results in a pre-prorennin molecule with sixteen additional amino acids compared to purified prorennin (The prorennin B amino acid sequence was published by B. Foltmann et al. *Proc. Nat. Acad. Sci. USA* 74 2321-2324 (1977) and B. Foltmann et al *J. Biol. Chem.* 254 8447-8456 (1979); the nucleotide sequencing data of Table 9 is the first indication for the existence of pre-prorennin). Together, the two recombinant f1 phages 293-207 and 293-118/37 carry the DNA sequence for the entire pre-prorennin A molecule. The prorennin portion of the pre-prorennin A differs from prorennin B at amino acid #290 (aspartate in rennin A and glycine in rennin B as described by Foltmann et al [see above]; amino acid position numbering is that of Foltmann). An asparagine codon is shown at amino acid position #204 while Foltmann reported an aspartate at that position; however, this may be an amino acid sequencing error since the amides of aspartate and glutamate are difficult to distinguish from their acid forms, while nucleotide sequencing can readily distinguish the codons.

The cloned rennin gene represented by phage 293-118/37 was used to investigate properties of the bovine genomic copy or copies of the rennin gene. These experiments were done by hybridizing cloned rennin DNA labelled with $^{32}$P by the method of nick-translation (P. W. J. Rigby, M. Dieckmann, C. Rhodes, and P. Berg [1977] *J. Mol. Biol.* 113, 237-251) to bovine DNA cut with various restriction enzymes, separated with an agarose gel and transferred to a nitrocellulose membrane according to the method of Southern (E. M. Southern [1975] *J. Mol. Biol.* 98, 503-517). The results indicate that restriction endonuclease cleavage of the bovine DNA with enzymes such as SacI and Bgl I, which do not cut the cloned pre-prorennin cDNA sequence, nevertheless frequently yields more than one band of DNA which will hybridize to the rennin sequence. This suggests (a) that the genomic copy of rennin information contains additional DNA, presumably intervening sequences, which contain restriction enzyme sites not found in rennin cDNA, or (b) that more than one rennin gene exists in the genome and some restriction enzymes cut between the copies. This latter possibility was eliminated by hybridizing restriction cut bovine genomic DNA with $^{32}$P-labelled probes derived from the 5' and 3' ends of the cloned rennin cDNA. These results, using restriction endonucleases EcoRI and BamHI for example, are consistent with a single genomic copy of rennin coding information. This means that A and B forms of rennin observed by B. Foltmann et al (*J. Biol. Chem.* 254, 8447-8456 [1979]) are most likely the products of two different alleles of the rennin gene. Furthermore, the bovine genomic copy of the rennin gene contains intervening sequences, and in that respect the genomic copy is different from our cloned cDNA gene which is identical to the messenger RNA for pre-prorennin.

6. Expression of Prorennin in Yeast

Recombinant f1 phage CGF 293-207 RFI DNA (40 μg) was cut with Hind III (N. E. Biolabs, 15 units) and BglII (N. E. Biolabs, 14 units) for one hour at 37° C. in a 103 μl reaction volume as described previously. The restriction cut DNA was applied to a preparative horizontal agarose gel, and the 435 bp 293-207 piece was excised and eluted by freezing and crushing the agarose chunk. After ethanol precipitation, the DNA was redissolved in water and about 1 μg was partially cut with HhaI (N. E. Biolabs, 0.06 units) for 15 minutes at 37° C. to obtain the 190 bp HhaI to BglII piece containing the pR start. This DNA fragment was isolated by gel as described Previously and rendered blunt-ended by treatment with DNA polymerase I (Boehringer Mannheim, 14 units) in a 30 μl reaction containing 60 mM tris-HCl, pH 7.5, 8 mM MgCl$_2$, 10 mM dithiothreitol, 1 mM ATP and 0.2 mM of each deoxynucleotide triphosphate for 30 minutes at room temperature. The DNA was phenol extracted and ethanol precipitated.

A synthetic oligonucleotide bearing an Xba I restriction endonuclease sequence ending with ATGG, (i.e., CCATCTAGATGG) was synthesized by the triester method (K. Itakura, et al., *J. Biol. Chem.* 250 4592 [1975]) by Collaborative Research, Inc. and 5 μg was kinased with γ32-p-ATP using 6 units T4 polynucleotide kinase (P-L Biochemicals) in a 35 μl reaction containing Tris HCl pH 7.6, 10 mM MgCl$_2$, 10 mM 2-mercaptoethanol and 2 nmoles ATP. This 5'-labelled oligonucleotide (22 p-moles ends) was added to about 0.5 pmoles of the 190 bp fragment with buffer plus 500 units of T$_4$ DNA ligase (N. E. Biolabs). The reaction was incubated at 15° C. for one hour then at 4° C. overnight, and then diluted with four volumes of 180 mM NaCl, 7 mM MgCl$_2$ and 5 mM Tris HCl, pH 8. After heating at 65° C. for five minutes, the DNA was treated with 12 units of XbaI restriction endonuclease (5 units additionally were added after one hour for a total of 1.5 hours of digestion). Finally, the oligonucleotide monomers were removed from the linkered 190 bp DNA by gel electrophoresis (7% polyacrylamide gel). The DNA fragment was eluted from the acrylamide chunk by soaking in buffer for 24 hours. The DNA was ethanol precipitated, redissolved in 15 μl of water and incubated in a ligation reaction containing 0.5 μg of CGF12-f1 vector opened at XbaI site and then treated with alkaline phosphatase as described previously. Aliquots of the ligation reaction were used to transform competent cells of strain LG90 as described above. The transformed cells were plated on tryptone-yeast extract plates containing f1 sensitive cells (JM101). Several phage plaques were picked and small cultures of each were grown to provide a small amount of RF1 DNA. Restriction endonuclease digestion (XbaI and HaeIII) and agarose gel electrophoresis revealed that some phage clones carried the desired 190 bp fragment in the desired orientation (5'-end of prorennin gene adjacent to the single EcoRI site of CGF12). One such isolate was named CGF21.

About 10 μg of the CGF21 DNA was cut with PstI (N. E. Biolabs, 7 units) for 45 minutes at 37° C. in a 40 ml reaction as previously described. The PstI cut DNA was then cut with EcoRI (N. E. Biolabs, 10 units) for 45 minutes at 37° C. The 100 bp PstI/EcoRI fragment was isolated by acrylamide gel. The plasmid pBR322 (~8 μg) was cut with EcoRI (N. E. Biolabs, 7.5 units) and HindIII (N. E. Biolabs, 7.5 units) for one hour at 37° C. in a 30 μl reaction volume. The resulting Hin dIII/EcoRI fragment (4.3 Kb) was purified by agarose gel. CGF293-118/37 DNA (10 μg) was cut with PstI (N. E. Biolabs, 8 units) and HindIII (N. E. Biolabs, 10 units) for one hour at 37° C. in a 30 μl reaction volume.

The 1.1 kb PstI/HindIII DNA fragment was purified by agarose gel. The three DNA fragments were joined in a tri-molecular ligation reaction to yield pCGE68. The tri-molecular ligation (reaction volume 27 μl) contained approximately equal molar proportions of the three fragments totaling 1.5 μg DNA. The ligation reaction was carried out with 400 units T4 DNA ligase (N. E. Biolabs) at 12° C. for 8 hours. Aliquots of the ligation reaction were used to transform competent cells of strain LE392 as described. Analysis of the plasmid DNA by restriction enzyme digestion (PstI, XbaI, BglII and KpnI) and agarose gels revealed that some isolates carried the desired plasmid pCGE68. This plasmid contains the DNA encoding Met-prorennin.

The pCGE68 DNA (10 μg) was cut with XbaI (N. E. Biolabs, 10 units for 2 hours at 37° C. After precipitation with ethanol, the DNA was rendered blunt ended by treatment with S1 nuclease (30 units) for 30 minutes at 37° C. After phenol extraction and ethanol precipitation the DNA was incubated with 5'-phosphorylated SalI linker (Collaborative Research, 2.5 μg). The linker had been kinased with γ-$^{22}$P-ATP usinq 2.5 units of T$_4$ polynucleotide kinase (P-L Biochemicals) in a 10 μl reaction containing 10 Tris-HCl, pH 7.6, 10 mM Mg Cl$_2$ 10 mM 2-mercaptoethanol and 0.12 nmoles ATP. The linker was ligated to the blunt-ended pCGE68 DNA in a 25 μl reaction for 8 hours at 14° C. The resulting ligated DNA containing a SalI linker was used to transform competent cells of strain BNN45. Restriction enzyme (SalI) and agarose gels were used to identify the desired plasmid, pCGE91.

The construction of prorennin in yeast was now begun. The first yeast vector of interest, pCGS128, was made from a ligation of three pieces. First, pCGE91 was cut with SalI (N. E. Biolabs, 10 units) for 3 hours at 37° C. Tnis DNA fragment was then rendered blunt-ended by treatment with DNA polymerase I (Boehringer/Mannheim, 10 units) in a 50 μl reaction containing 10 mM Tris-HCI, pH7.5, 8 mM MgCl$_2$, 10 mM dithiothreitol, and 0.2 mM of each deoxynucleotide triphosphate for one hour at room temperature. The blunt ended DNA was then ethanol precipitated, redissolved and cut with HindIII (N. E. Biolabs, 7.5 units) for 1 hour at 37° C. The 1200 bp blunt-ended SalI/HindIII DNA fragment was purified by agarose gel electrophoresis. The next DNA fragment containing the necessary components of a shuttle vector was purified from pCGS40. This latter vector was cut with EcoRI and HindIII and the resulting 7000 bp fragment was purified by agarose gel electrophoresis. The third DNA fragment containing the P$_{GAL}$promoter came from pBM125 (courtesy of R. Davis, Stanford University) which was cut with BamHl, blunted with DNA polymerase I plus all four deoxynucleotide triphosphates, then cut with EcoRI to yield a 820 bp piece designated P$_{GAL}$125. The nucleotide sequences depicting the promoter lengths are shown in Table 1. The three pieces of DNA (1200 bp from pCGE91, SalI blunt-ended/HindIII, 7000 bp from pCGS 40 EcoRI/HindIII, and 820 bp from P$_{GAL}$125 were ligated together using equimolar amounts of the fragments in a 25 μl reaction containing T$_4$ DNA ligase (Collaborative Research, 2 blunt-ended units) and appropriate buffers and ATP and incubated for 18 hours at 14° C.

The ligated DNA was used to transform competent cells of strain CGE129. Analysis of the plasmid DNA by restriction enzyme digestion and agarose gel revealed isolates which carried the desired plasmid pCGS128. DNA of pCGS128 was used to transform yeast strain CGY150. The transformed spheroplasts were selected. Western protein blot analyses revealed that the yeast strain carried prorennin (∼0.02%).

In order to increase the expression of prorennin an additional construction was carried. The pCGS128 DNA was cut with HindIII. A fragment (pRB58) from the 3' end of the SUC 2 gene was cut with HindIII, made blunt-ended with E. coli DNA polymerase I and then SalI linkers were ligated on. The resulting fragment was cut with SalI and Bam/ H1 to produce a gel purified 1 kb DNA fragment which was ligated into p CGS40 cut with BamH1 and SalI.

The resulting vector, pCGS1108, was cut at HpaI and SalI, made blunt with E. coli DNA polymerase I and gel purified. HindIII linker (Collaborative Research, 10 nucleotides long) were ligated to the DNA fragment which was then cut with HindIII and gel purified to produce a 650 bp fragment which was ligated into the HindIII site of pCGS128 to produce pCGS168.

Figure 6:
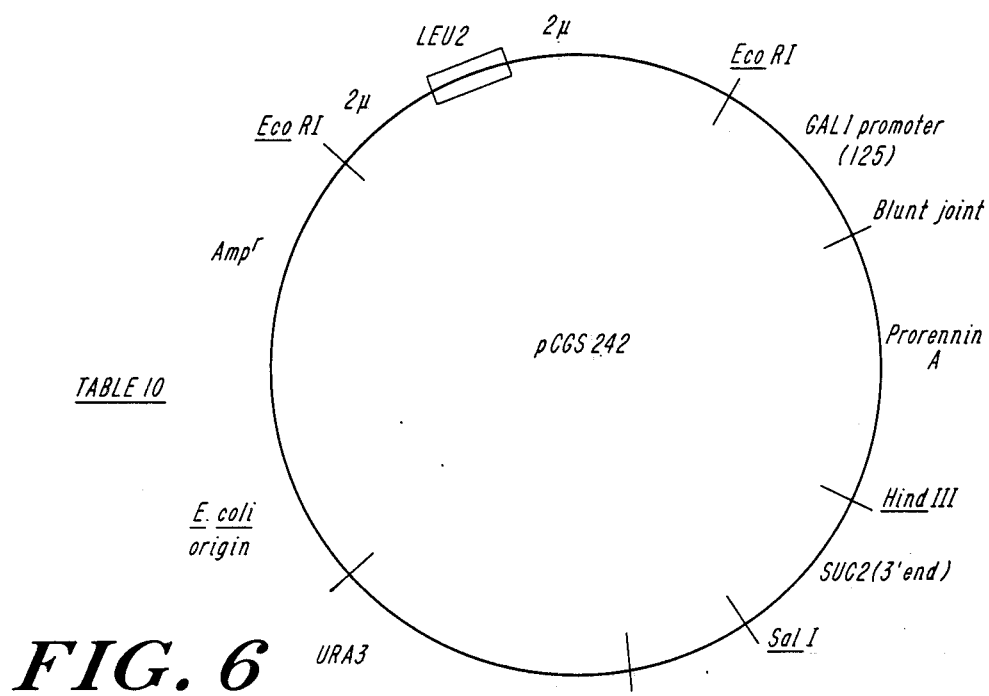

A partial EcoRI and SalI cut was made of the pCGS168 vector to isolate a 2.6 kb DNA fragment containing P$_{GAL}$125 and prorennin. A partial EcoRI cut was made from pJDB219 to produce a gel purified 2.3 kb fragment containing the LEU2 gene on a 2 μDNA fragment. These two DNA fragments were ligated together with a EcoRI/SalI digest of Ylp5 (containing selection for URA3) to yield pCGS241 and pCGS242 (FIG. 6). The difference in structure is due to the two orientations of the 2.3 kb fragment. Both vectors were separately used to transform CGY150. Analysis of the plasmid DNA by restriction enzyme digestion and agarose gel revealed the desired plasmid with the level of prorennin expression via western analysis was increased to 0.2% of the soluble protein. The protein demonstrated milk clotting activity after conversion to rennin.

Strain CGY461 bearing plasmid pCGS242 is on deposit with the American Type Culture Collection (ATCC), Accession Number 20662, deposited February, 1983.

EXAMPLE 4

Production of Pre-prorennin

Steps 1 through 5 of Example 3 were repeated for this experiment.

6. Expression of Preprorenin in Yeast

Recombinant fl phage CGF 293/207 RFI DNA (20 μg) was cut with AvaII (N. E. Biolabs, 5 units) in a 100 μl reaction. The 256 bp AvaII fragment was purified by gel electrophoresis and made blunt-ended with E. coli DNA polymerase I Klenow fragment. After phenol extraction and ethanol precipitation, the DNA was ligated with HindIII linker (Collaborative Research, CAAGCTTG) then cut with HindIII (N. E. Biolabs, 15 units) and BglII (N. E. Biolabs, 3.6 units). A 245 bp fragment was purified by gel electrophoresis containing part of the preprorennin gene. Plasmid pCGS28 DNA (U.S. patent application Ser. No. 325, 481 filed Dec. 1, 1981 by B. Alford, et al.) was cut with BglII (N. E. Biolabs, 5 units) and SalI (N. E. Biolabs, 10 units) and a 1000 bp DNA fragment containing the rest of the preprorennin gene was purified by gel. These two DNA fragments were ligated together with pBR322 cut with HindIII (N. E. Biolabs, 12 units) and SalI (N. E. Biolabs, 8 units). This vector was used to transform competent E.coli cells and the resulting restriction enzyme analysis of plasmid DNA from several *E. coli* clones revealed the desired plasmid pCGE63 in *E. coli* strain CGE130.

The preprorennin gene was used to construct PCGS148 which is p$_{GAL126}$ preprorennin. Plasmid pCGE63DNA was cut with HindIII and SalI to yield a 1200 bp fragment containing preprorennin DNA. A EcoRI/HindIII double digest was carried out on pRB118 to obtain a 850 bp fragment containing P$_{suc2}$. These fragments were ligated in a tri-molecular reaction as described with an EcoRI/SalI fragment of pCGS40 which imports the characteristics of a shuttle vector. The mixture was used to transform competent CGE129 *E. coli* cells. Clones of *E. coli* carrying the desired plasmid pCGS64 were identified by restriction digestion of plasmid DNA from several transformants.

A BglII/SalI fragment (~9 kb) of pCGS64 was purified by gel electrophoresis and contained part of the preprorennin gene, as well as the pCGS40 EcoRI/SalI fragment. A BglII/Xho-I 3600 bp fragment of pCGE74 containing the rest of preprorennin fused at the SmaI site in preprorennin gene most of the *E. coli* β-galactosidase gene was ligated to the piece from pCGS64. Transformation was carried out and restriction analyses showed the presence of the desired yeast plasmid pCGS81.

The P$_{SUC2}$ was removed from pCGS81 by restriction first with HindIII followed by filling in with *E. coli* DNA polymerase I Klenow fragment. The opened plasmid was then restricted with EcoRI and the large fragment minus P$_{suc2}$ was gel purified. The P$_{GAL126}$ was obtained by restriction of pBM126 (courtesy R. Davis, Stanford, University). The plasmid pBM126 was cut with BamH1 and filled in with *E.coli* DNA polymerase I Klenow fragment and then cut with EcoRI to yield the desired 750 bp P$_{GAL126}$. These two fragments were ligated together to get pCGS148, which contains P$_{GAL126}$ preprorennin 'Z (where 'Z represents a portion of β-galactosidase gene).

Figure 7:
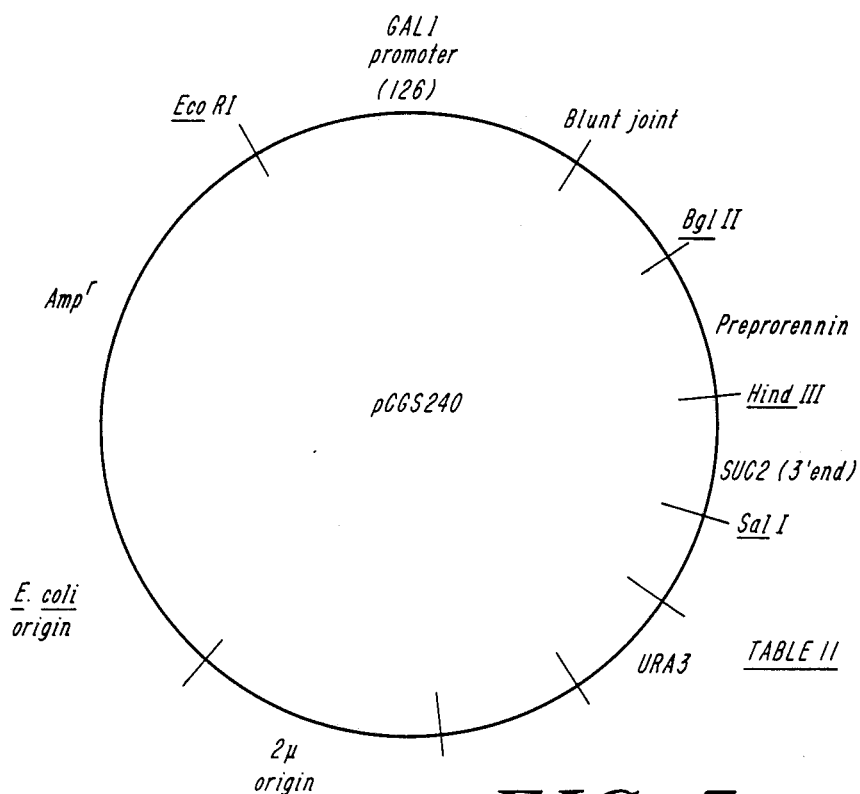

A 1000 bp piece of DNA was obtained by digesting pCGS148 with EcoRI and BglII. In addition, the BglII/SalI 1800 bp fragment of pCGS168 was gel purified. These two fragments were ligated with the 8kb EcoRI/SalI fragment of pCGS 40 in excess. Transformation of competent *E. coli* CGE129 was carried out and restriction analysis revealed clones carrying the desired plasmid pCGS240 (FIG. 7). Plasmid DNA prepared from *E. coli* carrying pCGS240 was used to transform yeast strain CGY150. Yeast strain CGY457 resulted from that transformation and carries plasmid pCGS240. The level of expression of protein from the GAL1 promoter as demonstrated by western hybridization with rennin antibody was ~0.2% of the soluble protein.

Strain CGY457 bearing plasmid pCGS240 is on deposit with the American Type Culture Collection (ATCC), Accession Number 20661, deposited February, 1983.

While the specific embodiments of the invention have been shown and described, many variations are possible. For example, the present invention is mainly concerned with the use of a GAL1 promoter in the production of polypeptides such as bovine growth hormone, interferon, prorennin and pre-prorennin in yeast. Obviously, other protein products can be obtained and expressed using a GAL1 promoter of this invention in the operative relationship defined. Such polypeptides may be enzymes or other biologically active proteins. The foregoing examples are illustrative of the operation of such a mechanism.

What is claimed is:

1. Yeast strain as deposited in the American Type Culture Collection under Accession Number 20643, Strain Designation CGY196.

2. Yeast strain as deposited in the American Type Culture Collection under Accession Number 20661, Strain Designation CGY457.

3. Yeast strain as deposited in the American Type Culture Collection under Accession Number 20662, Strain Designation CGY461.

4. Yeast strain as deposited in the American Type Culture Collection under Accession Number 20663, Strain Designation CGY528.

5. A DNA segment containing a GAL1 promoter linked to a gene other than the galactokinase gene for directing the expression of the gene within a yeast cell, wherein said GAL1 promoter has the following nucleotide sequence:

```
         10            20           30
GAATTCGACAGGTTATCAGCAACACAGTCA 40            50           60
TATCCATTCTCAATTAGCTCTACCACAGTG 70            80           90
TGTGAACCAATGTATCCAGCACCACCTGTA 100           110          120
ACCAAAACAATTTTAGAAGTACTTTCACTT 130           140          150
TGTAACTGAGCTGTCATTTATATTGAATTT 160           170          180
TCAAAAATTCTTACTTTTTTTTTGGATGGA 190           200          210
CGCAAAGAAGTTTAATAATCATATTACATG 220           230          240
GCATTACAACCATATACATATCCATATACA 250           260          270
TATCCATATCTAATCTACTATATGTTGTGG 280           290          300
TATGTAAAGAGCCCCATTATCTTAGCCTAA 310           320          330
AAAAACCTTCTCTTTGGAACTTTCAGTAAT 340           350          360
ACGCTTAACTGCTCATTGCTATATTGAAGT 370           380          390
ACGGATTAGAAGCCGCCGAGCGGGTGACAG 400           410          420
CCCTCCGAAGGAAGACTCTCCTCCGTGCGT 430           440          450
CCTCGTCTTCACCGGTCGCGTTCCTGAAAC 460           470          480
GCAGATGTGCCTCGCGCCGCACTGCTCCGA 490           500          510
ACAATAAAGATTCTACAATACTAGCTTTTA 520           530          540
TGGTTATGAAGAGGAAAAATTGGCAGTAAC 550           560          570
CTGGCCCCACAAACCTTCAAATGAACGAAT 580           590          600
CAAATTAACAACCATAGGATGATAATGCGA
```

-continued

```
         610          620          630
TTAGTTTTTTAGCCTTATTTCTGGGGTAAT 640          650          660
TAATCAGCGAAGCGATGATTTTTGATCTAT 670          680          690
TAACAGATATATAAATGCAAAAACTGCATA 700          710          720
ACCACTTTAACTAATACTTTCAACATTTTC
```

-continued

```
         730          740
GGTTTGTATTACTTCTTATTC AAATGTAAT
                                  750

AAAAGTATCAACAAAAAATT
         760          770

GTTAATATACCTCTATACTTTAACGTCAAG
         780          790          800

GAGAAAAAACCCCGGATCC
         810          820
```

* * * * *